US008263763B2

(12) United States Patent
Wei et al.

(10) Patent No.: US 8,263,763 B2
(45) Date of Patent: Sep. 11, 2012

(54) CHEMICALLY MODIFIED POLYAMINOSACCHARIDE BY A HYDROCARBYL SULTONE COMPOUND

(75) Inventors: I-Chien Wei, Kaohsiung (TW); Kung-Hsing Lee, Kaohsiung (TW); Hsien-Ming Hung, Kaohsiung (TW); Ning Tsao, Kaohsiung (TW); Meng-Hui Hsu, Kaohsiung (TW); Shan-Ying Lin, Kaohsiung (TW); Ya-Hui Huang, Feng-Shan (TW)

(73) Assignee: Taiwan Hopax Chemicals Manufacturing Company, Ltd., Feng-Shan, Kaohsiung Hsien (TW)

( * ) Notice: Subject to any disclaimer, the term of this patent is extended or adjusted under 35 U.S.C. 154(b) by 256 days.

(21) Appl. No.: 11/157,132

(22) Filed: Jun. 20, 2005

(65) Prior Publication Data

US 2006/0025583 A1    Feb. 2, 2006

Related U.S. Application Data

(63) Continuation-in-part of application No. 10/871,890, filed on Jun. 18, 2004.

(51) Int. Cl.
*C08B 37/00* (2006.01)
(52) U.S. Cl. ............ 536/124; 536/20; 514/55; 514/62
(58) Field of Classification Search ............ 536/20, 536/124; 514/55, 62
See application file for complete search history.

(56) References Cited

U.S. PATENT DOCUMENTS

| | | | |
|---|---|---|---|
| 2,755,275 A | 7/1956 | Cushing et al. | 260/211 |
| 3,911,116 A | 10/1975 | Balassa | 424/180 |
| 3,914,413 A | 10/1975 | Balassa | 424/180 |
| 4,134,412 A | 1/1979 | Gross et al. | 132/7 |
| 4,202,881 A | 5/1980 | Gross et al. | 424/70 |
| 4,223,023 A | 9/1980 | Furda | 424/180 |
| 4,394,373 A | 7/1983 | Malette et al. | 424/95 |
| 4,532,134 A * | 7/1985 | Malette et al. | 514/55 |
| 4,647,536 A | 3/1987 | Mosbach et al. | 435/177 |
| 4,954,619 A | 9/1990 | Lang et al. | 536/20 |
| 5,098,733 A | 3/1992 | Kyogoku et al. | 426/573 |
| 5,129,877 A | 7/1992 | Gallo et al. | 600/12 |
| 5,166,187 A | 11/1992 | Collombel et al. | 514/21 |
| 5,208,159 A | 5/1993 | Toda et al. | 435/252.1 |
| 5,229,504 A | 7/1993 | Hayashi | 536/20 |
| 5,336,415 A | 8/1994 | Deans | 210/725 |
| 5,374,627 A | 12/1994 | Ito et al. | 514/55 |
| 5,454,907 A | 10/1995 | Hayashi | 162/26 |
| 5,543,056 A | 8/1996 | Murcott et al. | 210/705 |
| 5,618,622 A | 4/1997 | Gillberg-Laforce et al. | 428/357 |
| 5,629,011 A | 5/1997 | Illum | 424/434 |
| 5,708,152 A * | 1/1998 | Lohmann et al. | 536/20 |
| 5,762,903 A | 6/1998 | Park et al. | 424/1.29 |
| 5,858,392 A | 1/1999 | Dumitriu et al. | 424/443 |
| 5,902,798 A * | 5/1999 | Gouda et al. | 514/55 |
| 5,976,550 A | 11/1999 | Engel et al. | 424/195.1 |
| 5,977,330 A | 11/1999 | Lohmann et al. | 536/20 |
| 6,060,429 A | 5/2000 | Ben-Shalom et al. | 504/116 |
| 6,200,619 B1 | 3/2001 | Nakamura et al. | 426/321 |
| 6,238,720 B1 | 5/2001 | Popper et al. | 426/574 |
| 6,242,099 B1 | 6/2001 | Grandmontagne et al. | 428/402.2 |
| 6,391,318 B1 | 5/2002 | Illum et al. | 424/278.1 |
| 6,413,910 B1 | 7/2002 | Vasiljevich et al. | 504/140 |
| 6,451,773 B1 | 9/2002 | Oester et al. | 514/55 |
| 6,461,635 B2 | 10/2002 | Zimmerman et al. | 424/443 |
| 6,495,142 B2 | 12/2002 | Sakai | 424/195.16 |
| 6,497,904 B2 | 12/2002 | Singh | 424/488 |
| 6,497,927 B1 | 12/2002 | Kim et al. | 427/601 |
| 6,503,527 B1 | 1/2003 | Whitmore et al. | 424/422 |
| 6,521,268 B2 | 2/2003 | You et al. | 424/725 |
| 6,562,802 B2 | 5/2003 | Johansson et al. | 514/55 |
| 6,638,918 B2 | 10/2003 | Davison et al. | 514/55 |
| 2002/0177577 A1 | 11/2002 | Hung et al. | 514/55 |
| 2002/0189022 A1 | 12/2002 | Chang | 8/115.51 |
| 2003/0104020 A1 | 6/2003 | Davison et al. | 424/401 |
| 2003/0114881 A1 | 6/2003 | Stalemark et al. | 606/201 |
| 2003/0134120 A1 | 7/2003 | Kim et al. | 428/375 |
| 2003/0176306 A1 | 9/2003 | McKechnie | 510/379 |
| 2003/0203084 A1 | 10/2003 | Iverson et al. | 426/302 |

FOREIGN PATENT DOCUMENTS

| | | |
|---|---|---|
| DE | 34 22 227 A1 | 3/1986 |
| DE | 3432227 A1 * | 3/1986 |
| EP | 0 392 396 A2 | 10/1990 |
| GB | 838 709 | 6/1960 |
| JP | 63274457 | 11/1988 |
| JP | 2 240101 A | 9/1990 |
| JP | 4 103434 A | 4/1992 |
| JP | 5345712 | 12/1993 |
| JP | 6048917 | 2/1994 |
| JP | 2001 131591 A | 5/2001 |
| KR | 163098 B1 * | 11/1998 |

OTHER PUBLICATIONS

Goodman and Gilman's "The Pharmacological Basis of Therapeutics", 10th Ed., 1996, p. 54-57.*  Kondo et al J. Chem. Engg. of Japan, 1997, 30(5), 846-851.*
Chen et al, Journal of Food Protection, 1998, 61(9), 1124-1128.*
Kondo, Kazio, et al., "Selective Adsorption of Metal Ions on Novel Chitosan-Supported Sulfonic Acid Resin", Journal of Chemical Engineering of Japan, vol. 30 No. 5, pp. 848-851, 1997.
Wolfrom. M.L., et al., "The Sulfonation of Chitosan", Contributed from the Department of Chemistry of The Ohio State University, pp. 1764-1766, Jul. 21, 1958.
Study on the Semi-IPN of Sulfonated Polyurethane and Chitosan, New Taiwan University, pp. 9-35, 2001.
Kondo et al.; Chemical Engineering Ring, vol. 43, No. 8; with English translation of relevant paragraph; pp. 7, 1998.

* cited by examiner

*Primary Examiner* — Shaojia Anna Jiang
*Assistant Examiner* — Ganapathy Krishnan
(74) *Attorney, Agent, or Firm* — Baker Botts L.L.P.

(57) ABSTRACT

This invention discloses chemically modified polyaminosaccharides, in particular chemically modified chitosans, in the molecular structure of which a predetermined proportion of the amino functional groups is sulfonated by the hydrocarbyl sultone compound via a covalent bond. Such chemically modified polyaminosaccharides may be produced by a process of sulfonating an un-modified polyaminosaccharide having amino functional groups by a hydrocarbyl sultone compound in the presence of an organic solvent under a suitable temperature. Chemically modified chitosans of this invention may be used in a variety of applications, including wound healing.

49 Claims, 12 Drawing Sheets

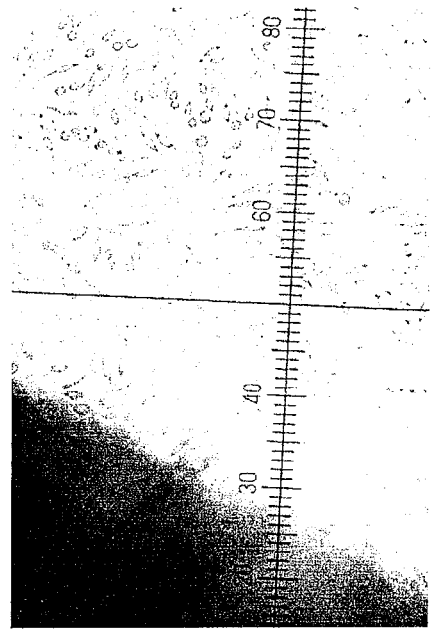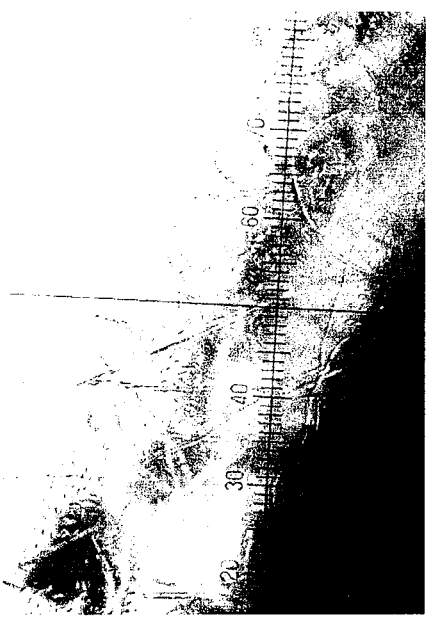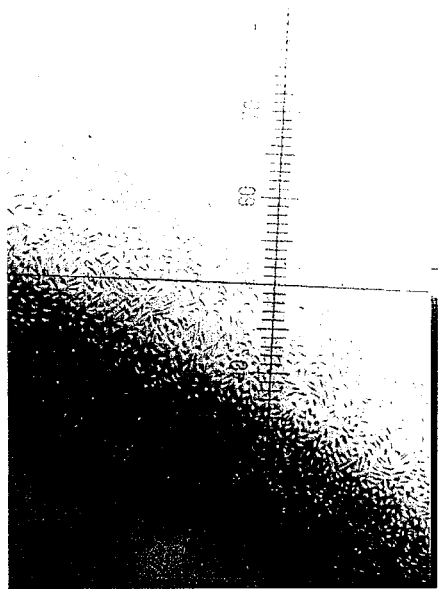
FIG. 9
FIG. 10

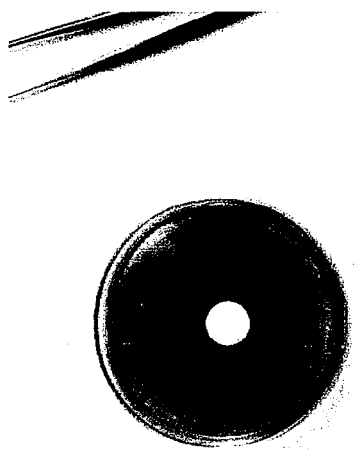
FIG. 11
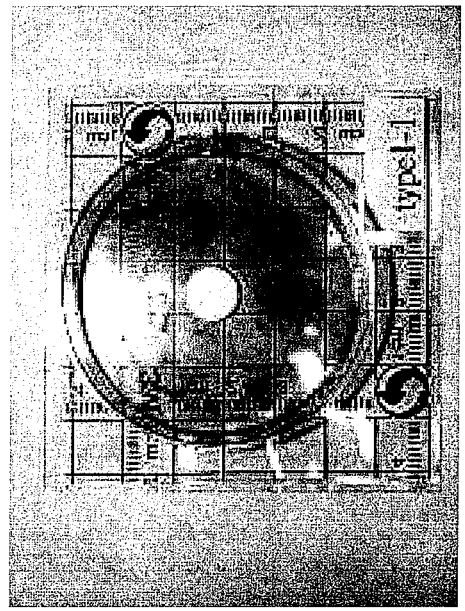
FIG. 12
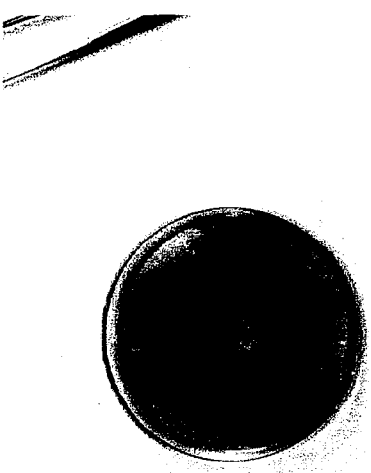

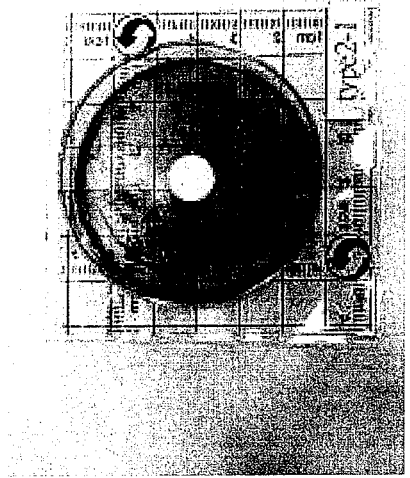
FIG. 13
FIG. 14
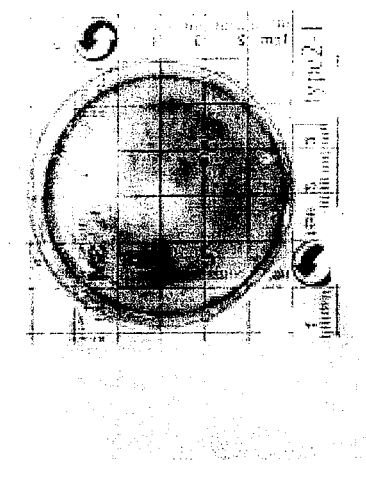

CHEMICALLY MODIFIED POLYAMINOSACCHARIDE BY A HYDROCARBYL SULTONE COMPOUND

CROSS-REFERENCE TO RELATED APPLICATION

This application is a continuation-in-part (CIP) application of U.S. patent application Ser. No. 10/871,890, entitled "Alkylsulfonated polyaminosaccharides" and filed on Jun. 18, 2004, the entire disclosure of which is incorporated herein by reference.

BACKGROUND OF THE INVENTION

1. Field of the Invention

This invention relates to chemically modified polyaminosaccharides, processes of making such molecules, and their uses, particularly in wound healing. Specific aspects of this invention relate to chemically modified chitosans by a hydrocarbyl sultone compound.

2. Description of the Related Art

Polyaminosaccharides are of considerable interest in a number of fields ranging from medicine and agriculture to water treatment and cleaning products. However, the use of such molecules is somewhat limited by difficulties in dissolving them in water. Thus, various approaches have been used to increase solubility of polyaminosaccharides in water.

Previous processes often involved adding an organic or inorganic acid to polyaminosaccharides to render them soluble in water. However, the resultant solution has a very acidic pH, thereby decreasing its usefulness in many biological applications. Increasing the pH of the solution tend to cause precipitation of the polyaminosaccharides.

Other processes have involved addition of a sulfonic acid group to the molecules of polyaminosaccharides. However, these processes have oftentimes resulted in serious degradation of the starting materials. In addition, such processes tend to produce a pool of modified polyaminosaccharides with high variability in important properties, such as polymer length and degree of substitution. While such modified polyaminosaccharides may exhibit increased water solubility, their use in applications benefiting from precise knowledge of polyaminosaccharide properties is either severely curtailed or requires additional processing.

Chitosan, which may be represented by the following chemical structure, is a polyaminosaccharide of particular interest in a number of applications. Like many polyaminosaccharides, chitosan may be readily harvested from naturally occurring materials. The primary source of chitosan is discarded shells of lobsters and crayfishes or shrimps, although it may also be obtained from the shells of crabs and other crustaceans as well as from insect shells and fungi. Chitosan is normally non-toxic and is compatible with the tissues and skins of a variety of living organisms, including human beings. However, like many other polyaminosaccharides, chitosan exhibits only limited solubility in water.

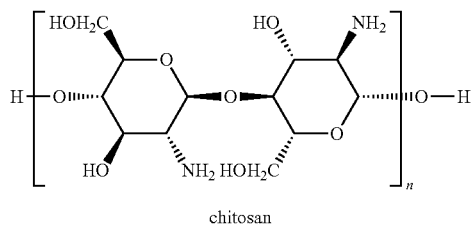

chitosan

Conventionally, the water solubility of chitosan may be increased by the addition of an acid. In addition, chitosan has also been sulfonated, which results in a molecule with a chemical structure similar to that of heparin, a powerful anticoagulant.

One previous process for sulfonating chitosan involves the use of chlorosulfonic acid as a sulfonating agent in an organic solvent of low polarity, such as pyrimidine. An organic base is subsequently added as an acid receptor for the sulfonation reaction. However, chlorosulfonic acid is not easy to use, and it sulfonates not only at the amino groups of the polyaminosaccharide, but also at other sites, such as the hydroxy groups. Besides, the need to supply an acid receptor complicates the reaction. Overall, the reaction is difficult to carry out and oftentimes results in a low yield of poorly characterized and unpredictable product.

Other known processes for sulfonating chitosan utilize alkyl sultones, such as 1,3-propane sultone, which are considerably easier to use than chlorosulfonic acid. In this aspect, reference may be made to, e.g., Kazuo Kondo et al., *Journal of Chemical Engineering of Japan* (1997), Vol. 30, No. 5, pp. 846-851, and a 2001 master thesis, entitled "Study on the semi-IPN of sulfonated polyurethane and chitosan," which was authored by Yung-Hsin Lin, Chemical Engineering Institute, National Taiwan University. However, these processes involve the addition of alkyl sultones to chitosan in an aqueous acetic acid solution. The water molecules react readily with alkyl sultones in the aqueous solution and hydrolyzes them, thus resulting in a substantial loss of the same. Furthermore, the hydrolysis of the alkyl sultones results in the formation of a highly acidic alkylsulfonic acid, which then causes the degradation of the chitosan. As a result, these processes require the use of large amounts of alkyl sultone and chitosan but give very poor yields. Therefore, these processes are not economical for industrial applications. In addition, because of degradation, the length of the resultant alkylsulfonated chitosan varies widely, even when a uniform starting material is used. The degree of sulfonation of the amino group by the used alkyl sultone also varies widely and cannot be reliably predicted from the outset. Besides, when a chitosan was sulfonated based on the aforesaid processes, a predominant portion of bonding between the amino groups thereof and the alkyl sultone is actually ionic bonding, which can be readily disrupted by changes in the chemical environment. Although covalent bonding, which is much more stable, might occur, it is infrequent and does not represent a significant portion of the bonding between the amino groups of chitosan and the alkyl sultone. Finally, the applicants are unaware of any report in regard to the would-be properties and effects of the alkylsulfonated chitosan produced by these processes.

DE 3432227 A1 disclosed sulfopropyl derivatives of alkali chitins and chitosans of formula (I):

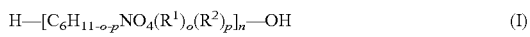

wherein $R^1$ represents —$CH_2$—$CH_2$—$CH_2$—$SO_3M$ (M=H, Na or K);

$R^2$ represents —(C=O)—$CH_3$;

n is integer from 50 to 10000;

o is a numeral from 0.05 to 4.0; and p is a numeral from 0.01 to 1.0.

DE 3432227 A1 disclosed that the aforesaid derivatives could be obtained from sulfonating alkali chitins or chitosans by 1,3-propane sultone with stirring (votexing) at a temperature of 10° C. to 80° C. and in the presence of an organic solvent (such as isopropanol (IPA) or acetone) for a period of 6 to 60 hrs. However, the three synthesis examples provided therein were conducted at a temperature of 25° C. or 45° C. for a period of 24 hrs or 48 hrs. respectively. In addition, in the three synthesis examples of DE 3432227 A1, IPA was the only solvent used in the sulfonation reaction, and acetone in fact was used as a precipitating agent in the product purification procedure.

According to the disclosure of DE 3432227 A1, one can obtain a composition of heterogeneous alkali chitin/chitosan molecules having a diversity of substitution patterns (i.e., the 1,3-propane sultone might be attached to either one or both of the —$NH_2$ group and —$CH_2OH$ group of each saccharide monomer of alkali chitin/chitosan molecules, and acetyl groups might still remain in some saccharide monomers).

However, at least for safety reasons, a composition of heterogeneous molecules is not desirable for the manufacture of medicinal products, cosmetic products and the like. In addition, the biological properties of the products obtained in the three synthesis examples of DE 3432227 A1, if any, were not actually tested.

DE 3432227 A1 is totally silent to the use of organic solvents other than isopropanol, as well as the use of sulfonating agents other than 1,3-propane sultone. A possible reason for DE 3432227 A1 to select isopropanol as the only solvent for the sulfonation reaction may be that 1,3-propane sultone is highly reactive and will immediately be hydrolyzed to alkylsulfonic acid upon contacting with water. Since the commercially available isopropanol has a very low water content (<1%), hydrolysis of 1,3-propane sultone by water can be avoided. This assumption may also explain at least in part the rationale for DE 3432227 A1 to select so low a reaction temperature (25° C. and 45° C.).

However, the applicants found from experimentation that when chitosan is chemically modified by 1,3-propane sultone in the presence of isopropanol at 25° C. for 24 hrs, the recovered product has no significant increase in weight, indicating no or very low attachment of 1,3-propane sultone to the saccharide monomers of chitosan molecules. When the sulfonation reaction was conducted at 45° C. for 48 hrs, while the recovered product has an increase in weight, it will form a gel-like product when treated with an ammonia solution$_{(aq)}$, just like the alkylsulfonated chitosan obtained in the comparative example described below, in which a 2% acetic acid solution is used as the solvent (see infra). Therefore, it is very likely that the sulfopropyl derivatives of chitosans produced according to DE 3432227 A1 have molecular structures in which the sulfopropyl groups derived from 1,3-propane sultone are attached to the free amino groups primarily via ionic bonding instead of covalent bonding.

Accordingly, there is still a need in the art to develop new methods for sulfonating polyaminosaccharides, in particular chitosans, and to explore the potential of the thus-obtained products in a variety of applications, e.g., in the manufacture of a product selected from the group consisting of a personal care product, a food product, a cleaning product, an agricultural product, a cosmetic product, a medicinal product, a medical device, a fabric product, a product for water-treatment, and a biochemical product.

SUMMARY OF THE INVENTION

Therefore, according to a first aspect, this invention provides a chemically modified polyaminosaccharide produced by a process of sulfonating an un-modified polyaminosaccharide having amino functional groups by a hydrocarbyl sultone compound in the presence of an organic solvent under a suitable temperature, such that in the molecular structure of the chemically modified polyaminosaccharide, a predetermined proportion of the amino functional groups is sulfonated by the hydrocarbyl sultone compound via a covalent bond.

In the second aspect, this invention provides a process for producing a chemically modified polyaminosaccharide, comprising:
forming a mixture by admixing an organic solvent with an un-modified polyaminosaccharide having amino functional groups;
sulfonating the un-modified polyaminosaccharide by adding a hydrocarbyl sultone compound to the mixture under a suitable temperature, such that in the molecular structure of the chemically modified polyaminosaccharide, a predetermined proportion of the amino functional groups is sulfonated by the hydrocarbyl sultone compound via a covalent bond; and
recovering the thus-formed chemically modified polyaminosaccharide.

In the third aspect, this invention provides a composition comprising a chemically modified chitosan produced by a process of sulfonating an un-modified chitosan having amino functional groups by a hydrocarbyl sultone compound in the presence of an organic solvent under a suitable temperature, such that in the molecular structure of the chemically modified chitosan, a predetermined proportion of the amino functional groups is sulfonated by the hydrocarbyl sultone compound via a covalent bond.

The chemically modified chitosan according to this invention has been found to have at least one of the following properties: promoting wound healing, inhibiting the growth of microorganisms, having no toxic effect to mammals, having no skin irritation effect to mammals, having no inflammatory effect to mammals, absorbing UV light, maintaining skin hydration, histocompatibility to human skin, and having the effect in controlling the release of volatile molecules. Therefore, it is contemplated that the chemically modified chitosan according to this invention is useful in a variety of industrial applications, including in the manufacture of a product selected from the group consisting of a personal care product, a food product, a cleaning product, an agricultural product, a cosmetic product, a medicinal product, a medical device, a fabric product, a product for water-treatment, and a biochemical product.

BRIEF DESCRIPTION OF THE DRAWINGS

The above and other features and advantages of the present invention will become apparent in the following detailed description of the preferred embodiments with reference to the accompanying drawing, of which:

FIG. 9 shows the cellular morphology of mouse fibroblasts L929 grown around an experimental dressing, i.e. chitosan fibers, in which left panel: 100× magnification; and right panel: 1000× magnification;

FIG. 10 shows the cellular morphology of mouse fibroblasts L929 grown around an experimental dressing, i.e., an alkylsulfonated chitosan according to an embodiment of this invention, which has an 80% degree of sulfonation, in which left panel: 100× magnification; and right panel: 1000× magnification;

FIG. 11 shows the cytotoxicity of an experimental dressing, i.e., KALTOSTAT®, upon mouse fibroblasts L929 as detected by histological analysis (2% crystal violet stain), in which left panel: control group; and right panel: experimental group;

FIG. 12 shows the cytotoxicity of an experimental dressing, i.e., an un-modified chitosan sponge, upon mouse fibroblasts L929 as detected by histological analysis (2% crystal violet stain), in which left panel: control group; and right panel: experimental group;

FIG. 13 shows the cytotoxicity of an experimental dressing, i.e., chitosan fibers, upon mouse fibroblasts L929 as detected by histological analysis (2% crystal violet stain), in which left panel: left panel: control group; and right panel: experimental group;

FIG. 14 shows the cytotoxicity of an experimental dressing, i.e., an alkylsulfonated chitosan according to an embodiment of this invention, which has an 80% degree of sulfonation, upon mouse fibroblasts L929 as detected by histological analysis (2% crystal violet stain), in which left panel: control group; and right panel: experimental group;

DETAILED DESCRIPTION OF THE INVENTION

Figure 1:
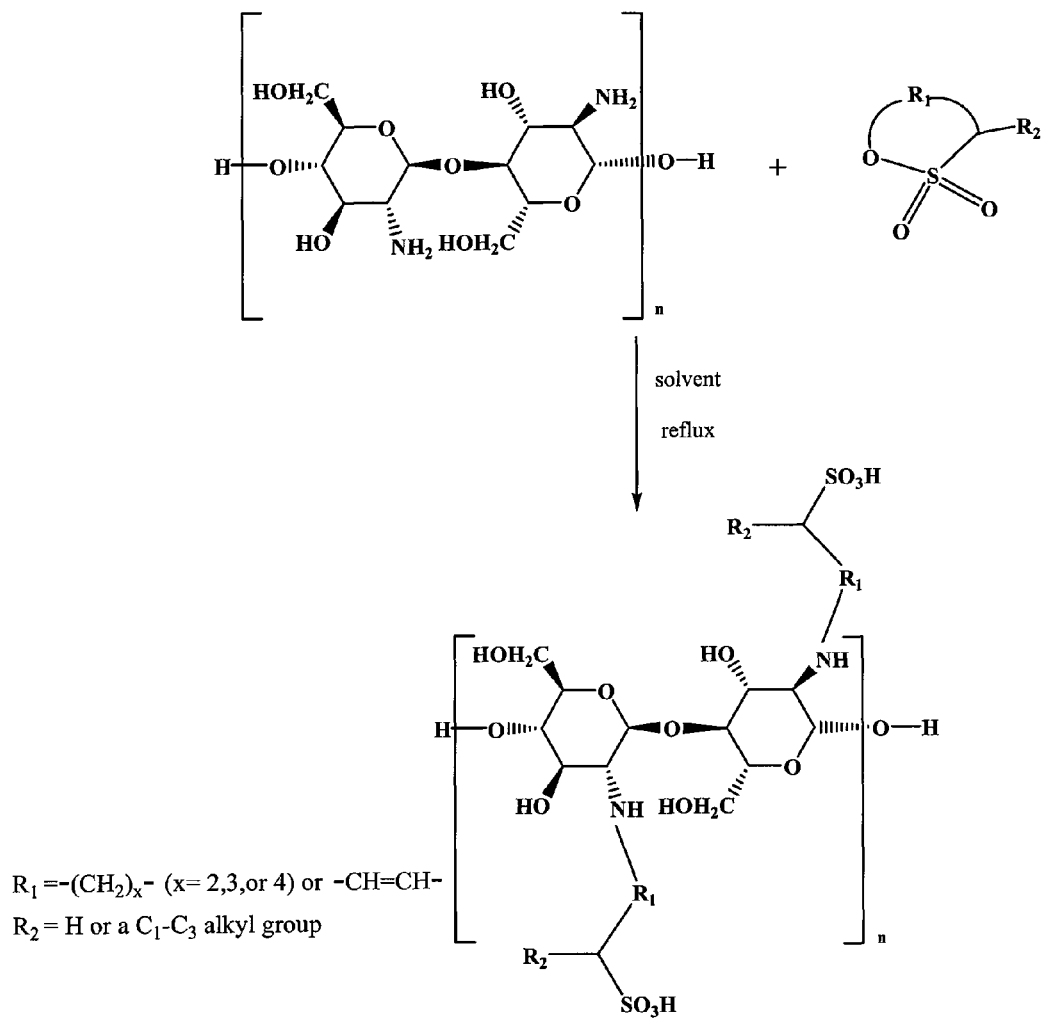
FIG. 1 schematically shows the synthesis of a chemically modified chitosan according to this invention.

This invention relates to chemically modified polyaminosaccharides and processes for producing them and their industrial applications. In selected embodiments, it relates to chemically modified chitosans.

In this invention, the applicants found that an un-modified polyaminosaccharide having amino functional groups could be sulfonated by a hydrocarbyl sultone compound in the presence of an organic solvent under a suitable temperature to form a chemically modified polyaminosaccharide, in the molecular structure of which a predetermined proportion of the amino functional groups is sulfonated by the hydrocarbyl sultone compound via a covalent bond.

Therefore, this invention provides a chemically modified polyaminosaccharide produced by a process of sulfonating an un-modified polyaminosaccharide having amino functional groups by a hydrocarbyl sultone compound in the presence of an organic solvent under a suitable temperature, such that in the molecular structure of the chemically modified polyaminosaccharide, a predetermined proportion of the amino functional groups is sulfonated by the hydrocarbyl sultone compound via a covalent bond.

This invention also provides a process for producing a chemically modified polyaminosaccharide, comprising:
  forming a mixture by admixing an organic solvent with an un-modified polyaminosaccharide having amino functional groups;
  sulfonating the un-modified polyaminosaccharide by adding a hydrocarbyl sultone compound to the mixture under a suitable temperature, such that in the molecular structure of the chemically modified polyaminosaccharide, a predetermined proportion of the amino functional groups is sulfonated by the hydrocarbyl sultone compound via a covalent bond; and
  recovering the thus-formed chemically modified polyaminosaccharide.

After the sulfonation reaction, the thus-formed chemically modified polyaminosaccharides may become less soluble or insoluble in the reaction mixture and may thus be readily recovered.

The chemically modified polyaminosaccharides according to this invention may have a length substantially identical to the un-modified polyaminosaccharide because no degradation of the un-modified polyaminosaccharide due to the hydrolysis of the hydrocarbyl sultone compound occurs. In addition, they are sulfonated almost exclusively on the amino functional groups, and the degree of sulfonation may substantially correspond to that predicted at the outset of the reaction.

The term "un-modified polyaminosaccharide" as used herein refers to a saccharide polymer, the molecular structure of which contains amino functional groups. The "un-modified polyaminosaccharide" suitable for use in this invention may include, but is not limited to, saccharide polymers obtained from natural sources or chemically synthesized molecules, e.g., chitosans, glycosaminoglycans (GAG) and the like.

The un-modified polyaminosaccharide may be pre-processed to influence the results of the sulfonation reaction. For example, it may be deacetylated to allow access to the amino functional groups. It may also have protective groups to limit the degree of sulfonation, although this is not necessary in many embodiments. Reactive groups may be provided to facilitate other desirable reactions with the hydrocarbyl sultone compound.

The un-modified polyaminosaccharide may be of any size, but in specific embodiments, it may have a molecular weight between 300 and 1,500,000. More specifically the un-modified polyaminosaccharide may be classified into four groups of different molecular weights: (1) very low molecular weight molecules having a MW less than 10,000; (2) low molecular weight molecules having a MW ranging from 10,000 and 35,000; (3) high molecular weight molecules having a MW ranging from 35,000 and 140,000; and (4) very high molecular weight molecules having a MW ranging from 140,000 and 1,500,000.

In selected embodiments of the present invention, the un-modified polyaminosaccharides may include a chitosan. The chitosan may be selected from the group consisting of α-chitosan, β-chitosan, linear chitosan, branched chitosan, and combinations thereof. In addition, the chitosan may be obtained from deacetylation of a chitin purified from natural sources, such as the shells of crustaceans, the exoskeletons of insects, and the cell walls of fungi, and it may have a degree of deacetylation ranging from 50% to 100%. Sulfonation on the amino groups renders the chitosan more hydrophilic by virtue of formation of sulfonate groups, and may stabilize the molecule.

The applicants surprisingly found that, since the sulfonation reaction according to this invention was carried out in the presence of a selected organic solvent under a suitable temperature, it greatly favors the attachment of the hydrocarbyl sultone compound to the —NH$_2$ group than the —CH$_2$OH group on each saccharide monomer of chitosan molecules. In addition, in some specific embodiments, the sulfonation reaction was carried out under the reflux temperature of the organic solvent, which is usually higher than 45° C. As a result, no hydrolysis of the hydrocarbyl sultone compound in particular 1,3-propane sultone, may take place due to the presence of a small amount of water contained in the commercially available organic solvent.

According to this invention, the organic solvent may be a highly polar solvent. For example, the organic solvent is selected from the group consisting of an alcohol, an ether, an ether alcohol, and combinations thereof. In certain embodiments, the organic solvent is selected from the group consisting of methanol, ethanol, isopropanol, butanol, methoxypropanol, and combinations thereof. In specific embodiments, the solvent may have less than 10% water.

When methanol is used as the organic solvent, it can provide additional advantages due to the high polarity thereof. Specifically, an un-modified chitosan of low to very high MW may become swollen when admixed with methanol, thereby increasing the penetration of the hydrocarbyl sultone compound to contact with the saccharide monomers of the un-modified chitosan. In addition, sulfonation of chitosan by the hydrocarbyl sultone compound will predominantly take place at the —NH$_2$ group than the —CH$_2$OH group (sulfonation reactivity: —NH$_2$>>—CH$_2$OH) on the saccharide monomers of the un-modified chitosan. Therefore, when methanol is used as the organic solvent, the sulfonation reaction for un-modified chitosan of low to very high MW can be carried out at a temperature ranging from about 25° C. to about 67° C.

When an un-modified chitosan of very low MW is used, the preferred organic solvent is one that will not render the un-modified chitosan soluble, e.g., 1-methoxy-2-propanol.

In some specific embodiments of this invention, the sulfonating reaction is conducted under a reflux temperature of the organic solvent in use. The reflux temperature may correspond to the boiling temperature of the mixture. For example, the reflux temperature may be between 50° C. to 150° C., and more preferably between 60° C. to 140° C. In a preferred embodiment, methanol is used as the organic solvent, and the reflux temperature may be set to around 65~67° C. In another preferred embodiment, n-butanol is used as the organic solvent, and the reflux temperature may be set to around 117~120° C. In a further preferred embodiment, isopropanol is used as the organic solvent, and the reflux temperature may be set to around 82~85° C. In a further preferred embodiment, 1-methoxy-2-propanol is used as the organic solvent, and the reflux temperature may be set to around 110~115° C.

The hydrocarbyl sultone compound is added to the mixture of the un-modified polyaminosaccharide and the organic solvent, either gradually or all at once. The hydrocarbyl sultone compound normally reacts almost exclusively with the amino functional groups of the un-modified polyaminosaccharide, with little to no reaction with the hydroxy groups. Furthermore, the hydrocarbyl sultone compound is normally primarily sulfonated to the amino functional groups of the un-modified polyaminosaccharide via a covalent bond, which is far more resistant to changes in the chemical environment than an ionic bond. Ionic bonds are the most common type of bonds formed in many previous processes as described above. The present invention may result in at least 50%, at least 60%, at least 70%, at least 80%, at least 90%, at least 95%, or at least 98% of sultone-amino group bonds being covalent bonds.

According to this invention, the hydrocarbyl sultone compound is selected from alkyl sultones and alkenyl sultones. In certain embodiments, the hydrocarbyl sultone compound has a formula of:

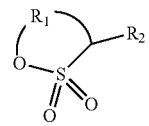

wherein

R$_1$ is selected from —(CH$_2$)$_x$— (where x is an integer of 2 to 4) and —CH=CH—; and R$_2$ is selected from H and a C$_1$-C$_3$ alkyl group.

In more specific embodiments, the hydrocarbyl sultone compound is selected from 1,3-propane sultone, 1,3-propene sultone, 1,4-butane sultone, 2,4-butane sultone, and combinations thereof.

When the used hydrocarbyl sultone compound is 1,4-butane sultone, preferably, the sulfonation of the un-modified polyaminosaccharide is conducted in the presence of an organic solvent other than isopropanol and under a reflux temperature ranging from 110° C. to 150° C.

More preferably, when 1,4-butane sultone is used to sulfonate chitosan, the sulfonation reaction is conducted in the presence of n-butanol or 1-methoxy-2-propanol under a reflux temperature ranging from 110° C. to 130° C. After a reaction time of 6-8 hrs, an alkylsulfonated chitosan in a yield of 55%-92% could be obtained.

Selection of a hydrocarbyl sultone compound and any combination of two more hydrocarbyl sultone compounds may be based on the desired properties and uses of the chemically modified polyaminosaccharides to be produced. For example, selection of the hydrocarbyl sultone compound may be based on the need to perform further chemistry on the polyaminosaccharides, which may be facilitated by the presence of a specific alkyl group or influenced by the steric effect of a large alkyl group.

The relative amounts of the un-modified polyaminosaccharide and the hydrocarbyl sultone compound used in the reaction may be selected to give a desired degree of sulfonation upon the thus-formed chemically modified polyaminosaccharide.

According to this invention, the degree of sulfonation may be influenced by the amount and nature of the hydrocarbyl sultone compound added, and in many embodiments, substantially all of the added hydrocarbyl sultone compound reacts with the un-modified polyaminosaccharide. The length of the un-modified polyaminosaccharide also influences the degree of sulfonation, as a longer molecule will require a larger amount of the hydrocarbyl sultone compound for a given degree of sulfonation when compared to a shorter molecule. The length of the un-modified polyaminosaccharide may be readily determined based on various measurements known in the art, such as molecular weight. Reaction temperature, gradual versus immediate addition of the hydrocarbyl sultone compound, and the reaction time may additionally influence the degree of sulfonation upon the obtained chemically modified polyaminosaccharide. Therefore, the degree of sulfonation obtained according to this invention tends to be consistent in many embodiments, and is predictable through routine experimentation with various un-modified polyaminosaccharides and hydrocarbyl sultone compounds.

According to this invention, the used amount of the hydrocarbyl sultone compound relative to the number of moles of the amino functional groups of the un-modified polyaminosaccharide is controlled so that the recovered chemically modified polyaminosaccharide has a predetermined degree of sulfonation ranging from 5% to at least 90%, preferably ranging from 10% to 80%. In selected embodiments, the degree of sulfonation of the chemically modified polyaminosaccharides is between 5% and 60%, or between 30% and 40%. In other selected embodiments, the degree of sulfonation of the chemically modified polyaminosaccharides may be at least 50%, at least 60%, at least 70%, at least 80%, at least 90%, or at least 95%.

In selected embodiments, the hydrocarbyl sultone compound is used in an amount ranging from one fourth to four times the number of moles of the amino functional groups of the un-modified polyaminosaccharide. In more specific embodiments, the hydrocarbyl sultone compound is used in an amount ranging from one half to two times the number of moles of the amino functional groups of the un-modified polyaminosaccharide.

After the sulfonation reaction, the thus-formed chemically modified polyaminosaccharide may be recovered by conventional purification methodologies, such as filtration, washing, drying, precipitation and/or crystallization. For example, it may be removed from the reaction mixture by filtration and then dissolved in water or another solvent, followed by precipitation or crystallization. In addition, because in some cases the resultant mixture after sulfonation treatment may become somewhat viscous, a certain amount of the organic solvent may be added to the resultant mixture so as to facilitate the isolation and purification of the desired product. In many embodiments of this invention, the thus-formed chemically modified polyaminosaccharide is recovered in a quite high yield, such as at least 50%, at least 80%, at least 90%, at least 95%, or even at least 99%.

The chemically modified polyaminosaccharide according to this invention may have a size that is normally accepted in the relevant field of use. In specific embodiments, the size of the chemically modified polyaminosaccharide generally corresponds to that of the un-modified polyaminosaccharide because the sulfonation reaction does not cause substantial degradation of the un-modified polyaminosaccharide.

In addition, since according to this invention, the degree of sulfonation of the un-modified polyaminosaccharide, in particular chitosan, can be predetermined, the chemically modified polyaminosaccharide derived therefrom may have a certain portion of the amino functional groups which are not sulfonated by the hydrocarbyl sultone compound. Such unreacted amino functional groups can be subjected to other treatments that render the chemically modified polyaminosaccharide suitable for use in the manufacture of medicinal products and the like.

The chemically modified polyaminosaccharide of this invention may be converted to a metal salt form by subjecting it to an alkaline treatment using a metal hydroxide aqueous solution. In some specific embodiments, the metal hydroxide aqueous solution is an aqueous solution of a metal hydroxide selected from NaOH, KOH, $NH_4OH$, $Mg(OH)_2$, $Ca(OH)_2$, and combinations thereof.

The chemically modified polyaminosaccharides of this invention may be non-toxic and biocompatible. They may be formed into a variety of forms, such as films, non-woven structures, aqueous solutions, powders and so forth. They may be used for a variety of purposes such as those described elsewhere in the present application, and may be supplied and used in any manner suitable for a given application.

Specifically, some chemically modified polyaminosaccharides of the present invention may be used for medical devices, personal care products, cosmetic products, oral care products, odor control products, agricultural products, products for water treatment, cleaning products, biochemical products, contact lens cleaning solutions, fabric products, medicinal products, etc. In order to facilitate these uses, they may be dissolved in water or an aqueous solvent to form solutions of different viscosities. They may also be used to form films or three-dimensional structures. Although the chemically modified polyaminosaccharide of this invention may be in a variety of forms for long-term storage, it is preferably stored in a powdered or lyophilized form so as to avoid degradation and other problems associated with storage.

While any suitable polyaminosaccharide may be used in this invention, a number of specific embodiments relate to the use of chitosan. More specifically, chitosan may be reacted with a hydrocarbyl sultone compound as schematically shown in FIG. 1. Based on this reaction scheme, if 100 g of chitosan having a molecular weight of approximately 161 is used, the amounts of 1,3-propane sultone indicated in Table 1 may be used to obtain the indicated degree of sulfonation. Table 1 shows that the degree of sulfonation of chitosan by 1,3-propane sultone is approximately in a linear relationship to the used amount of 1,3-propane sultone.

TABLE 1

The correlation of the used amount of 1,3-propane sultone to the degree of sulfonation of chitosan (M.W. 161) in a methanol solvent.

| Degree of sulfonation* | Amount of 1,3-propane sultone |
|---|---|
| 0 | 0 |
| 10 | 7.6 g |

TABLE 1-continued

The correlation of the used amount of 1,3-propane sultone to the degree of sulfonation of chitosan (M.W. 161) in a methanol solvent.

| Degree of sulfonation* | Amount of 1,3-propane sultone |
|---|---|
| 30 | 22.8 g |
| 70 | 53.1 g |
| 80 | 60.7 g |

*Expressed as percentage of available amino functional groups occupied by 1,3-propane sultone after sulfonation.

Based on the obtained results, it is clear that the degree of sulfonation of the chemically modified chitosan can be easily controlled as desired.

The chemically modified chitosan of this invention may be structurally similar to heparin. It has been found to have at least one of the following properties: promoting wound healing, inhibiting the growth of microorganisms, having no toxic effect to mammals, having no skin irritation effect to mammals, having no inflammatory effect to mammals, absorbing UV light, maintaining skin hydration, histocompatibility to human skin, and having the effect in controlling the release of volatile molecules.

When added into water with heating and stirring, it can be completely dissolved to form a transparent, light yellow aqueous solution with weak acidity (pH 5 to 6). The viscosity of the solution may be adjusted by the added amount of the chemically modified chitosan.

The chemically modified chitosan may also be formed into a transparent, elastic film. In certain exemplary embodiments, the elastic film may be produced by dissolving the chemically modified chitosan of this invention in a solvent, such as water, followed by removing the solvent, which may be effected by, e.g., heating the solution in an oven. In a specified embodiment, the solution is placed in an oven for one day. The thickness of this film may be varied by, e.g., controlling the concentration of the solution.

Various forms of the chemically modified chitosan may be used in a variety of manners, such as medical applications, including wound healing, disinfectants, water treatment, enzyme immobilization, and cosmetics. When in a film form, it may be used, inter alia, in medicine, medical devices, cosmetics and food.

The chemically modified chitosan of this invention may be used in the manufacture of a fabric product. The fabric product may be selected from the group consisting of a woven fabric, a knitted fabric, a non-woven fabric, and combinations thereof. In addition, the fabric product is made of nano-fibers. As an example, the chemically modified chitosan of this invention may be formed into weaves of nano-fibers similar to those formed from chitosan as disclosed in U.S. Pat. No. 6,638,918. It may then be put to similar uses. In addition, microcapsules made of the chemically modified chitosan of this invention may be formed and used in a manner similar to that described for chitin in U.S. Pat. No. 6,242,099. Hydrogels may be formed as described using chitosan as the cationic polysaccharide in U.S. Pat. No. 5,858,392. Finally, the chemically modified chitosan of this invention may be used to coat natural fibers as described in U.S. 2003/0134120.

The chemically modified chitosan of this invention has been proven to have the ability of inhibiting the growth of streptomycin-resistant *Staphylococcus aureus*, *E. coli*, *Pseudomonas aeruginosa* and *Candida albicans*, *Malassezia furfur*, *Malassezia pachydermatis* and *Propionibacterium acnes*, and may be able to inhibit or kill various other harmful microorganisms.

In a specific embodiment, the minimum inhibiting concentration (MIC) of an alkylsulfonated chitosan produced according to this invention is 0.38 mg/mL for streptomycin-resistant *Staphylococcus aureus*, 0.094 mg/mL for *E. coli* CCR 10675, 0.38 mg/mL for *Pseudomonas aeruginosa* CCRC 12450, and 0.19 mg/mL for *Candida albicans* CCRC 20511. These minimum inhibiting concentrations are generally lower than those of a corresponding un-modified chitosan. Therefore, the alkylsulfonated chitosan may be used in place of chitosan in applications where anti-microbial effects are desirable to obtain a better product.

Anti-microbial effects are largely independent of the size of the chemically modified chitosan, the degree of sulfonation, or the used hydrocarbyl sultone compound. Specifically, because of its anti-microbial properties, the chemically modified chitosan may be used in the manufacture of personal care products, such as a skin care product, a hair care product, a nail polish, an oral care product, an odor control product, and a contact lens cleaning solution; food products, such as a preserving agent, a food wrapping film, a health food, a dietary food, a food coating, a gellish food product, a weight-loss agent, and a food additive; cleaning products; agricultural products, such as a feed additive, an animal food additive, a plant care product, a fertilizer, a grass cultivator, a disease inhibitor, and an anti-fungal agent; cosmetic products, such as a beauty pack, an anti-aging cream, an anti-acne cream, a make-up, a facial cleansing product, and a maintenance product; medicinal products, such as an antibacterial agent, an anti-fungal agent, an anti-inflammatory agent, an anti-tumor agent, an anti-cholesterol agent, an anti-viral agent, a drug carrier, a vaccine, a microcapsule, a hydrogel, a fibrin adhesive, and a fibrin sealant; and medical devices, such as a radiation therapy device, a leukocyte removal device, an artificial vascular graft or vascular patch. The chemically modified chitosan of this invention may also be used in the manufacture of a biochemical product, such as an enzyme purifier, an enzyme holder, an exchangeable resin, and a TLC material; and a product for water-treatment, such as a heavy metal absorber, a lipid absorber, and a protein absorber.

For example, the chemically modified chitosan of this invention may be used in place of chitosan in combination with elecampane as an anti-bacterial and anti-inflammatory agent as described in U.S. Pat. No. 6,521,628. Fibers similar to anti-bacterial rayon fibers such as those described in U.S. Pat. No. 6,497,927 may be made using the chemically modified chitosan of this invention. Cleaning products, such as the mold and mildew remover of U.S. 2003/0176306, may be made with the alkylsulfonated chitosan of the present invention. The chemically modified chitosan of this invention may also be used to enhance resistance of plants to disease, as described in U.S. Pat. No. 6,413,910. It may also be used to control plant diseases as described in U.S. Pat. No. 6,060,429 and U.S. Pat. No. 5,374,627.

While the chemically modified chitosan of this invention is normally an anti-microbial agent, some organisms, such as those described in U.S. Pat. No. 5,208,159, may actually grow well in it. It may also be used to encapsulate cells not harmed by the anti-microbial effects as described for chitosan in U.S. Pat. No. 4,647,536.

Additionally, the chemically modified chitosan of this invention exhibits little to no toxicity to larger organisms, such as mammals. The acute oral toxicity ($LD_{50}$) amount for an alkylsulfonated chitosan produced according to this invention in rats is at least 5 g/kg, which is sufficient for it to be considered non-toxic. Additionally, the alkylsulfonated chitosan does not appear to have significant effects on the weight of rats when ingested regularly. Therefore, the chemically modified chitosan of this invention may be used as an additive in foods or medicines. For example, the chemically modified chitosan of this invention may be used in drug carriers or vaccines as described for un-modified chitosan in U.S. Pat. No. 6,497,904, cationic chitosan in U.S. Pat. No. 6,391,318, and various chitosans in U.S. Pat. No. 5,629,011. It may also be labeled with a radionuclide and used in radiation therapy as described for chitosan in U.S. Pat. No. 5,762,903. Use in place of the cationic derivatives of native chitosan in the anti-inflammatory, anti-viral and anti-fungal agent of U.S. Pat. No. 6,562,802 may also be possible. Cationic derivatives of native chitosan used for receptor-mediated delivery in U.S. Pat. No. 5,129,887 may also be replaced with the chemically modified chitosan of this invention.

Water treatment applications of chitosan have been described in U.S. Pat. No. 5,336,415 and U.S. Pat. No. 5,543,056, in which the chemically modified chitosan of this invention may also be used.

In yet another example, the chemically modified chitosan of this invention may be used in place of chitosan in oral care and odor control compositions such as those described in U.S. 2003/0104020. It may also be used in place of native chitosan in food coatings, preservatives, or gelled emulsions as described in U.S. 2003/0203084, U.S. Pat. No. 6,200,619, U.S. Pat. No. 4,223,023 and U.S. Pat. No. 6,238,720, or it may be used as a drug, weight loss agent, or food additive as described in U.S. Pat. No. 6,495,142, U.S. Pat. No. 5,098,733 and U.S. Pat. No. 5,976,550.

Further, the chemically modified chitosan of this invention does not irritate dermal tissue in rats or induce irregular or unusual growth. Thus, it is appropriate for use in personal care products, cleaning products, cosmetics and medical devices. The cosmetic product may be in a form selected from the group consisting of a gel, a cream, a grease, a spray, a foam, a non-woven fabric, a liquid, and a powder. For example, the chemically modified chitosan of this invention may be used with collagen to form beauty packs, as described for chitosan in JP 6,048,917 and JP 5,345,712. It may be used in place of chitosan in an anti-aging cream as described in U.S. 2003/0104020 or in anti-acne creams as described in U.S. Pat. No. 6,451,773. Use in place of chitosan in agents to aid in removal of adhesives from the epidermis as described in U.S. Pat. No. 6,461,635 is also possible.

In other applications, the chemically modified chitosan of this invention may be used in place of the cation residue of chitosan in a leukoreduction filter as described in U.S. Pat. No. 6,497,927. Other filtration media may also be made from chitosan as described in U.S. Pat. No. 5,618,622.

The chemically modified chitosan of this invention may also be used in place of the water-soluble salt of chitosan employed in the hair care products and methods disclosed in U.S. Pat. No. 4,202,881 and U.S. Pat. No. 4,134,412. It may also be used in place of differently modified chitosan to form nail polish as described in U.S. Pat. No. 4,954,619. Use of chitosans, which may be replaced with the chemically modified chitosan of this invention, in contact lens cleaning solutions is described in U.S. 2002/0177577.

Figure 5:
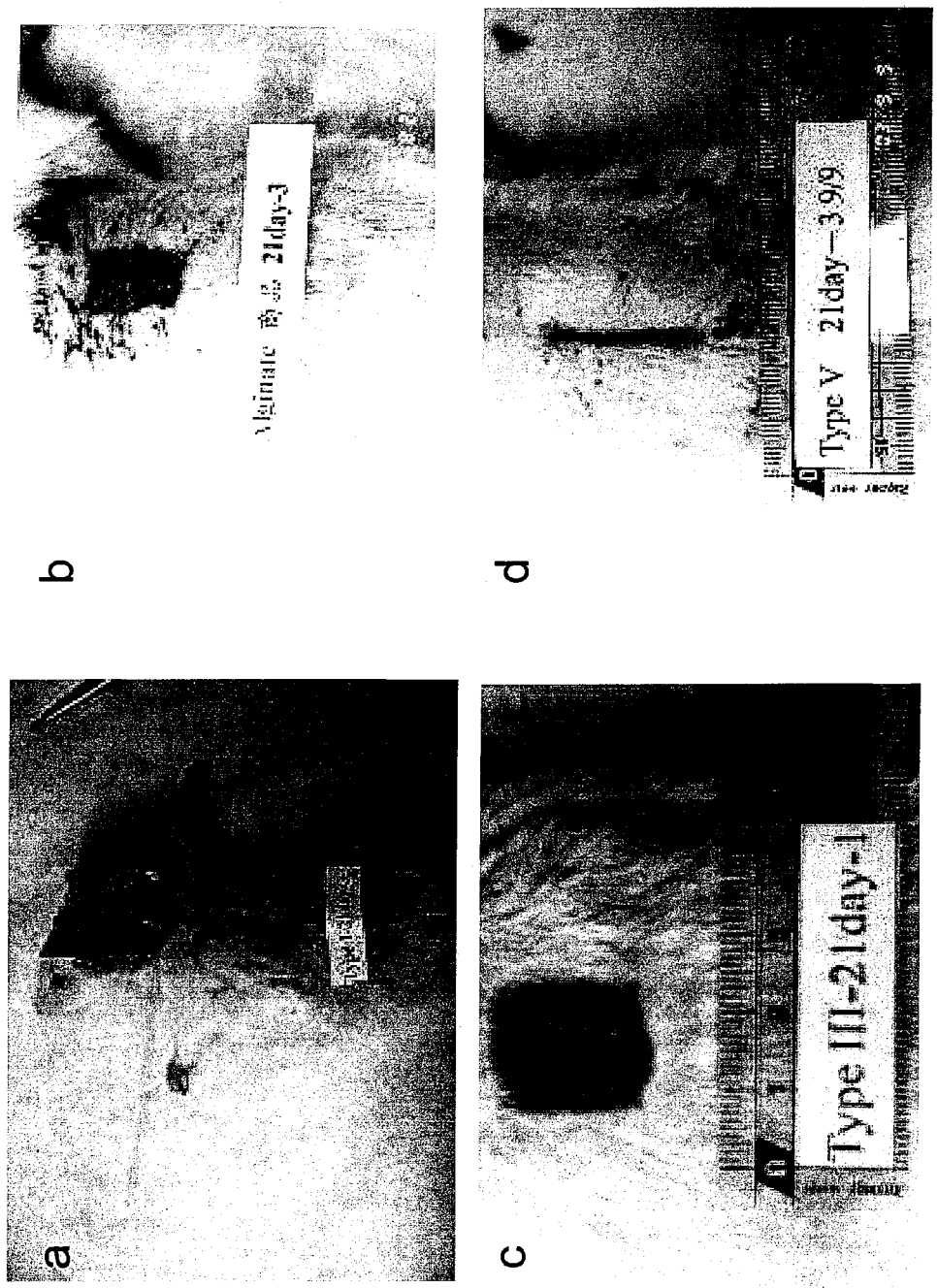
FIG. 5 shows the wound healing effects of four different dressings upon surgically wounded rats as observed on Day 21 after operation, in which panel a: alginate (KALTOSTAT®); panel b: an unmodified chitosan sponge; panel c: unmodified chitosan fibers; and panel d: an alkylsulfonated chitosan according to an embodiment of this invention, which has an 80% degree of sulfonation.

Chitosan has been previously explored as a potential wound dressing or anticoagulant. An alkylsulfonated chitosan according to an embodiment of this invention (FIG. 5, panel d) has been shown to be more effective in promoting wound healing than commercially available alginate wound dressings (KALTOSTAT®, ConvaTec, Ltd., UK)(FIG. 5, panel a), a chitosan sponge (FIG. 5, panel b), and chitosan fibers (Chinatex, Co. Ltd., Taiwan)(FIG. 5, panel c). As clearly shown in FIG. 5, the alkylsulfonated chitosan according to an embodiment of this invention, which has an 80% degree of sulfonation, produced remarkably superior wound healing in rats.

Thus, the chemically modified chitosan of this invention may be used in place of chitosan or other modified chitosan in a number of wound healing applications. For example, U.S. Pat. No. 3,911,116, U.S. Pat. No. 4,532,134 and U.S. Pat. No. 3,914,413 all discuss the use of chitin or modified chitin in the promotion of wound healing. The chemically modified chitosan of this invention, if used in the same manner as chitin in any of these three patents, would be expected to provide superior results. Similarly, the artificial skin described in U.S. Pat. No. 5,166,187 may be made with the chemically modified chitosan of this invention with expected improvements in the final product.

Accordingly, this invention provides a method of promoting wound healing in a mammal in need of such treatment, comprising applying the chemically modified chitosan of this invention to a mammal having a wound. In certain exemplary embodiments, the wound may include an open wound, a bleeding wound, an open ulcer, a wound caused by transplantation of a vascular graft or a vascular patch, a bleeding sutured area, a bleeding cardiac valve area, and combinations thereof. The chemically modified chitosan of this invention may be applied in a form selected from the group consisting of a film, a fiber, a sponge, a gel, a cream, a grease, a spray, a foam, a non-woven fabric, a liquid, and a powder. To effect wound healing, the chemically modified chitosan of this invention may be applied to a mammal having a wound for a period of at least 14-21 days or longer.

Application of the chemically modified chitosan of this invention can inhibit fibroplasia due to the healing of the wound of the mammal. Besides, when the wound of the mammal is a damaged vascular graft, the application of the chemically modified chitosan of this invention can promote tissue regeneration of the damaged vascular graft. Finally, the chemically modified chitosan of this invention may be used in place of the chitosan of U.S. 2002/0189022 to treat textiles after washing.

In all of the above examples, the chemically modified chitosan of this invention may be used in place of chitosan to achieve superior results. Thus, nowhere in the above discussion should be construed as indicating that the patents discussed encompass, teach or suggest any aspect of this invention.

The following examples are provided to further explain specific examples of the invention. They are given solely for the purpose of illustration and are not intended to represent all aspects of the invention in their entirety. Variations will be apparent to those skilled in the art.

EXAMPLES

Reagents Used

In the following examples, unless otherwise indicated, chitosan with a viscosity average molecular weight of between 10,000 and 200,000 was used. The chitosan used in the following examples generally includes poly(D-glucosamine) with about 75% to about 85% deacetylation. 1,3-propane sultone or 1,4-butane sultone was used as the hydrocarbyl sultone compound. The solvent for reaction was methanol, n-butanol or methoxypropanol.

Comparative Ex.

Production of an Alkylsulfonated Chitosan by a Previous Method

In this example, alkylsulfonated chitosan was synthesized according to a previous method described in a 2001 master thesis, entitled "Study on the semi-IPN of sulfonated polyurethane and chitosan," by Yung-Hsin Lin, Chemical Engineering Institute, National Taiwan University.

Six grams (g) of a chitosan powder (MW 140,000) was dissolved in 594 g of a 2 wt % acetic acid solution and filtered. The filtrate was placed in a four-neck flask and blanketed with nitrogen. The filtrate was brought to 30 degrees Celsius (° C.) and stirred at 200 revolutions per minute (rpm). Ninety milliliters (mL) of 1,3-propane sultone was added to the flask slowly, followed by stirring for 6 hours. The reaction product was then precipitated by addition of 1000 mL of acetone and separated by filtration. The product was then washed with a large amount of methanol and acetone for several times. It was subsequently dried in a vacuum oven. After drying, 9.3 g of a water-soluble alkylsulfonated chitosan was obtained with a yield of 88.15%. However, when sulfonating chitosan by this previous process, since the sulfonation reaction was conducted in an acidic condition and the pH of the reaction solution was sufficiently low, degradation of chitosan was observed (data not shown).

In order to determine the manner by which the 1,3-propane sultone was attached to the amino functional groups of the water-soluble alkylsulfonated chitosan produced according to this previous process, the following experiments were conducted.

Firstly, the sulfur content of the alkylsulfonated chitosan was determined to be equal to 9.79% by weight. Then, 2 g of the alkylsulfonated chitosan was added into 50 mL pure water, and the resultant solution was stirred to ensure that the added alkylsulfonated chitosan was dissolved in water. After standing overnight at room temperature, the solution was found to have a pH of 3.1. The solution was then added with an ammonia solution (20%) until the pH reached 11~12, which resulted in the formation of a gel-like product to separate out of the solution. Thereafter, the gel-like product was collected by filtration and washed with water and 50% methanol and finally with pure methanol. After drying the washed product in a vacuum oven (75° C.), a final product of 1.05 g was obtained, and the sulfur content thereof was measured to be 0.48% by weight. The detected reduction in sulfur content reveals that while chitosan may be sulfonated by 1,3-propane sultone to form an alkylsulfonated chitosan according to this previous process, an alkyl sulfonic acid group derived from 1,3-propane sultone was loosely attached to the amino functional groups of chitosan, and could be easily dissociated from the alkylsulfonated chitosan by the addition of an alkaline solution. It is therefore evident that in the alkylsulfonated chitosan produced by the previous process, the 1,3-propane sultone was attached to the amino functional groups primarily via ionic bonds.

Synthesis Ex. 1

Alkylsulfonated Chitosan Produced from the Reaction of a High MW Chitosan and 1,3-Propane Sultone 161 g of a high molecular weight chitosan (MW around 140,000) was placed in a flask, and 700 mL of methanol was added, followed by stirring. While heating the resultant mixture with stirring under a reflux temperature of 65-67° C., 122 g of 1,3-propane sultone was added slowly in drops. After all of the 1,3-propane sultone was added, the resultant mixture was refluxed for 4 further hours. The flask was then cooled to room temperature, and the product was collected by filtration and rinsed with methanol for several times. The product was then dried overnight in a vacuum oven. After drying, 282.1 g of an alkylsulfonated chitosan was obtained with a yield of 99.7%. In the present example according to this invention, since production of the alkylsulfonated chitosan was conducted in a near neutral condition (pH 5-6), no degradation of chitosan was observed.

In order to determine the manner by which the 1,3-propane sultone was attached to the amino functional groups of the alkylsulfonated chitosan produced according to this invention, the alkylsulfonated chitosan obtained in this example was subjected to experiments substantially identical to those described in the Comparative Example, so as to determine the variation of sulfur content before and after an alkaline treatment.

After the alkaline treatment, the sulfur content of the alkylsulfonated chitosan produced in this example was reduced from 8% to 5% by weight. This fact reveals that when chitosan was chemically modified according to this invention, an alkyl sulfonic acid group derived from 1,3-propane sultone was tightly attached to the amino functional groups of chitosan, and could not be easily dissociated from the alkylsulfonated chitosan by the addition of an alkaline solution. Therefore, it is reasonable to presume that in the alkylsulfonated chitosan produced according to this invention, the 1,3-propane sultone was attached to the amino functional groups primarily via covalent bonds.

In addition, as compared to the alkylfonated chitosan obtained from the Comparative Example, the alkylfonated chitosan produced in this example is readily soluble in water of neutral pH.

Synthesis Ex. 2

Alkylsulfonated Chitosan Produced from the Reaction of a Low MW Chitosan and 1,3-Propane Sultone 161 g of a low molecular weight chitosan (MW around 30,000) was placed in a flask, and 700 mL of methanol was added, followed by stirring. While heating the resultant mixture with stirring under a reflux temperature of 65-67° C., 122 g of 1,3-propane sultone was added slowly in drops. After all of the 1,3-propane sultone was added, the resultant mixture was refluxed for 4 further hours. The flask was then cooled to room temperature, and the product was collected by filtration and rinsed with methanol for several times. The product was then dried overnight in a vacuum oven. After drying, 280.2 g of an alkylsulfonated chitosan was obtained with a yield of 99.0%.

Synthesis Ex. 3

Alkylsulfonated Chitosan Produced from the Reaction of a Very Low MW Chitosan and 1,3-Propane Sultone 16.1 g of a very low molecular weight chitosan (MW around 10,000) was placed in a flask, and 200 mL of 1-methoxy-2-propanol was added, followed by stirring. While heating the resultant mixture with stirring under a reflux temperature of 110~115° C., 12.3 g of 1,3-propane sultone was added slowly in drops. After all of the 1,3-propane sultone was added, the resultant mixture was refluxed for 4 further hours. The flask was then cooled to room temperature, and the product was collected by filtration and rinsed with methanol for several times. The product was then dried overnight in a vacuum oven. After drying, 26.3 g of an alkylsulfonated chitosan was obtained with a yield of 92.9%.

Synthesis Ex. 4

Alkylsulfonated Chitosan Produced from the Reaction of a High MW Chitosan and 1,4-Butane Sultone In preliminary experiments, methanol and isopropanol were respectively used as the organic solvent to effect the sulfonation of chitosan (either high MW or low MW) by 1,4-butane sultone under a reflux temperature thereof. However, the chitosan failed to be sulfonated after a reaction time of 6~8 hrs. Therefore, n-butanol was selected to act as the organic solvent in this and the subsequent synthesis examples.

161 g of a high molecular weight chitosan (MW around 140,000) was placed in a flask, and 700 mL of n-butanol was added, followed by stirring. While heating the resultant mixture with stirring under a reflux temperature of 117~120° C., 136 g of 1,4-butane sultone was added slowly in drops. After all of the 1,4-butane sultone was added, the resultant mixture was refluxed for 8 further hours. The flask was then cooled to room temperature, and the product was collected by filtration and rinsed with methanol for several times. The product was then dried overnight in a vacuum oven. After drying, 252.5 g of an alkylsulfonated chitosan was obtained with a yield of 85%.

Synthesis Ex. 5

Alkylsulfonated Chitosan Produced from the Reaction of a Low MW Chitosan and 1,4-Butane Sultone 161 g of low molecular weight chitosan (MW around 30,000) was placed in a flask, and 700 mL of n-butanol was added, followed by stirring. While heating the resultant mixture with stirring under a reflux temperature of 117~120° C., 136 g of 1,4-butane sultone was added slowly in drops. After all of the 1,4-butane sultone was added, the resultant mixture was refluxed for 8 further hours. The flask was then cooled to room temperature, and the product was collected by filtration and rinsed with methanol for several times. The product was then dried overnight in a vacuum oven. After drying, 246.5 g of an alkylsulfonated chitosan was obtained with a yield of 83%.

In addition to n-butanol, 1-methoxy-2-propanol was tested in other experiments for sulfonating chitosan (either high MW or low MW) by 1,4-butane sultone. The reaction was conducted under a reflux temperature of around 118° C. for a period of 8 hrs. Thereafter, an alkylsulfonated chitosan was obtained with a yield of 55~65%.

Synthesis Ex. 6

Alkylsulfonated Chitosan Produced from the Reaction of a Very High MW Chitosan and 1,3-Propane Sultone 161 g of a very high molecular weight chitosan (MW around 500,000-1,500,000) was placed in a flask, and 700 mL of methanol was added, followed by stirring. While heating the resultant mixture with stirring under a reflux temperature of 65~67° C., 122 g of 1,3-propane sultone was added slowly in drops. After all of the 1,3-propane sultone was added, the resultant mixture was refluxed for 4 further hours. The flask was then cooled to room temperature and the product was collected by filtration and rinsed with methanol for several times. The product was then dried overnight in a vacuum oven. After drying, 280.4 g of an alkylsulfonated chitosan was obtained with a yield of 98.9%.

Synthesis Ex. 7

Production of a Chemically Modified Chitosan with a 32% Degree of Sulfonation from the Reaction of a Low MW Chitosan and 1,3-Propane Sultone 32.2 g of a low molecular weight chitosan (MW around 35,000) was placed in a 500 mL flask, and 300 mL of methanol was added, followed by stirring. While heating the resultant mixture with stirring under a reflux temperature of around 65° C., 8 g of 1,3-propane sultone was added slowly in drops. After all of the 1,3-propane sultone was added, the resultant mixture was refluxed for 4 further hours. The flask was then cooled to 20° C., and the reaction mixture contained therein was subjected to filtration to give a brown solid, which was subsequently rinsed with methanol for several times. The thus-collected product was then dried overnight in a vacuum oven. After drying, 35.4 g of a chemically modified chitosan with a 30% degree of sulfonation was obtained with a yield of 88%.

Synthesis Ex. 8

Production of a Chemically Modified Chitosan with a 40% Degree of Sulfonation from the Reaction of a Low MW Chitosan and 1,3-Propane Sultone 32.2 g of a low molecular weight chitosan (MW around 35,000) was placed in a 500 mL flask, and 300 mL of methanol was added, followed by stirring. While heating the resultant mixture with stirring under a reflux temperature of around 65° C., 9.8 g of 1,3-propane sultone was added slowly in drops. After all of the 1,3-propane sultone was added, the resultant mixture was refluxed for 4 further hours. The flask was then cooled to 20° C., and the reaction mixture contained therein was subjected to filtration to give a brown solid, which was subsequently rinsed with methanol for several times. The thus-collected product was then dried overnight in a vacuum oven. After drying, 38.22 g of a chemically modified chitosan with a 40% degree of sulfonation was obtained with a yield of 91%.

Synthesis Ex. 9

Production of a Chemically Modified Chitosan with a 50% Degree of Sulfonation from the Reaction of a Low MW Chitosan and 1,3-Propane Sultone 32.2 g of a low molecular weight chitosan (MW around 35,000) was placed in a 500 mL flask, and 300 mL of methanol was added, followed by stirring. While heating the resultant mixture with stirring under a reflux temperature of around 65° C., 12.2 g of 1,3-propane sultone was added slowly in drops. After all of the 1,3-propane sultone was added, the resultant mixture was refluxed for 4 further hours. The flask was then cooled to 20° C., and the reaction mixture contained therein was subjected to filtration to give a brown solid, which was subsequently rinsed with methanol for several times. The thus-collected product was then dried overnight in a vacuum oven. After drying, 40.8 g of a chemically modified chitosan with a 50% degree of sulfonation was obtained with a yield of 92%.

Synthesis Ex. 10

Production of a Chemically Modified Chitosan with an 80% Degree of Sulfonation from the Reaction of a Low MW Chitosan and 1,3-Propane Sultone 32.2 g of a low molecular weight chitosan (MW around 35,000) was placed in a 500 mL flask, and 300 mL of methanol was added, followed by stirring. While heating the resultant mixture with stirring under a reflux temperature of around 65° C., 19.5 g of 1,3-propane sultone was added slowly in drops. After all of the 1,3-propane sultone was added, the resultant mixture was refluxed for 4 further hours. The flask was then cooled to 20° C., and the reaction mixture contained therein was subjected to filtration to give a brown solid, which was subsequently rinsed with methanol for several times. The thus-collected product was then dried overnight in a vacuum oven. After drying, 48.08 g of a chemically modified chitosan with an 80% degree of sulfonation was obtained with a yield of 93%.

Experiment 1

Evaluation of the Anti-Microbial Effect of Chemically Modified Chitosan of this Invention In this experiment, an alkylsulfonated chitosan produced according to an embodiment of this invention (a high MW chitosan sulfonated with 1,3-propane sultone) was compared with an un-modified chitosan in terms of anti-microbial effects.

A 48-well plate was used for the present experiment although only the first 24 wells were used. All wells had a total volume of 1 mL. The first well received only 0.5 mL of sterilized water and 0.5 mL of Luria-Bertani broth (LB). The second well received 0.5 mL of a 3 wt % alkylsulfonated chitosan solution (prepared in a 2 wt % acetic acid solution) and 0.5 mL of a bacterial or yeast culture, which was prepared by admixing 1 mL of an overnight bacterial or yeast culture with 100 mL LB medium. The third well received 0.5 mL of the same alkylsulfonated chitosan solution and 0.5 mL of sterilized water. After mixing, 0.5 mL of the resultant solution in the third well was transferred to the fourth well, which was further added with 0.5 mL of sterilized water. A two-fold serial dilution was conducted from the third well to the twenty-fourth well in this manner. Thereafter, each of the third to twenty-fourth wells was added with 0.5 mL of the same bacterial or yeast culture. The 48-well plate was then placed at 37° C. for 24 hrs to allow the growth of the bacterial or yeast culture added in each well. A separate 48-well plate was used for each microorganism to be tested, including Streptomycin-resistant *Staphylococcus aureus*, *E. coli* CCRC 10675, *Pseudomonas aeruginosa* CCRC 12450 and *Candida albicans* CCRC 20511. In addition, an un-modified chitosan was tested for comparison.

Because the solution in each well would become more opaque due to an increase in microorganisms grown therein, the growth of microorganism could be detected by spectroscopy. Therefore, in this experiment, the anti-microbial effect of a tested compound (an alkylsulfonated chitosan of this invention or an un-modified chitosan) for a selected microorganism was expressed as minimum inhibitory concentration (MIC), which was determined by scanning the corresponding plate to detect the highest dilution/lowest concentration of the tested compound that prevents further growth of said microorganism. The obtained results are shown in Table 2.

TABLE 2

The minimum inhibitory concentrations (MIC) of an alkylsulfonated chitosan of this invention versus an un-modified chitosan for selected microorganisms

| | MIC (mg/mL) | |
|---|---|---|
| Microorganism | Alkylsulfonated Chitosan | Unmodified Chitosan |
| Streptomyacin-resistant *Staphylococcus aureus* | 0.38 mg/mL | 0.63 mg/mL |
| *E. coli* CCRC 10675 | 0.094 mg/mL | 0.625 mg/mL |
| *Pseudomonas aeruginosa* CCRC 12450 | 0.38 mg/mL | 1.25 mg/mL |
| *Candida albicans* CCRC 20511 | 0.19 mg/mL | 0.31 mg/mL |

The data shown in Table 2 clearly reveal that the alkylsulfonated chitosan of this invention exhibits superior anti-microbial effects than the un-modified chitosan. Therefore, it is contemplated that the chemically modified chitosan of this invention can act as an anti-microbial agent in the manufacture of a variety of products, e.g., personal hygiene products having anti-microbial effect against the above-indicated microorganisms, medicaments for treating diseases associated with at least one of the above-indicated microorganisms, etc.

Experiment 2

Evaluation of the Toxicity and Weight Loss Effect of Chemically Modified Chitosan of this Invention In this experiment, a powder of an alkylsulfonated chitosan produced according to an embodiment of this invention (a high MW chitosan sulfonated with 1,3-propane sultone) was used and mixed with animal feeds for oral administration to rats. A powder of an un-modified chitosan was also used as a control.

Twenty-four Wistar rats (7-week old) were divided into four groups. All rats were deprived of food overnight prior to commencement of the experiment. The four groups of rats were then respectively fed daily with the powder of the alkylsulfonated chitosan of this invention in different amounts, i.e., 2 g/kg, 3 g/kg, 4 g/kg and 5 g/kg, and the survival and body weight of the rats were monitored daily for 7 days. A powder of an un-modified chitosan was also used as a control.

Figure 2:
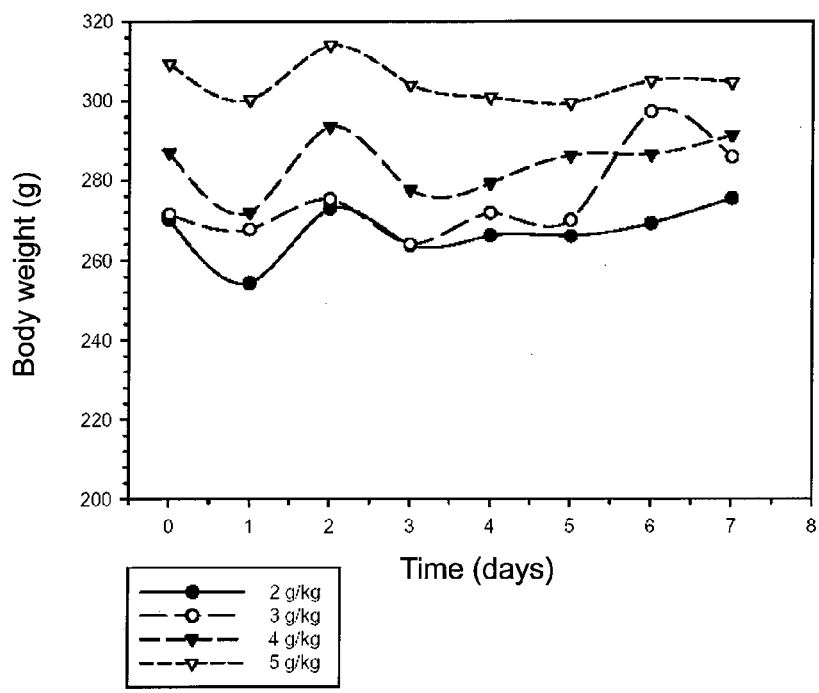
FIG. 2 is a graph showing the effects of different amounts of an alkylsulfonated chitosan powder according to an embodiment of this invention upon the body weights of rats (for each group, n=6)

This experiment was designed to determine the $LD_{50}$ value (the amount that produced death in 50% of the rats) for the alkylsulfonated chitosan. Like the un-modified chitosan, which is normally non-toxic to mammals, the oral administration of the alkylsulfonated chitosan of this invention did not cause the death of any rat during the experiment. Therefore, the $LD_{50}$ value of the alkylsulfonated chitosan of this invention is evidently well above 5 g/kg. In addition, referring to the experimental results shown in FIG. 2, the oral administration of the alkylsulfonated chitosan of this invention did not cause a significant loss of body weight in the tested rats, indicating that the alkylsulfonated chitosan of this invention is not harmful to animals.

Experiment 3

Evaluation of the Skin Irritation Effect of Chemically Modified Chitosan of this Invention In this experiment, a powder of an alkylsulfonated chitosan produced according to an embodiment of this invention (a high MW chitosan sulfonated with 1,3-propane sultone) was used.

The backs of Wistar rats (6-8 week old, 200-250 g) were shaved and allowed for recovery for 24 hours. The powder of the alkylsulfonated chitosan of this invention, in an amount of 0.25 g or 0.5 g, was added to a small amount of petroleum jelly and then applied onto a gauze pad having a size of 2.5×2.5 cm. The thus-prepared gauze pads were then fixed to the hair-shaved backs of the rats by ventilation tape. A control rat was treated with a gauze pad containing only petroleum jelly.

After application of a test gauze pad to a test area on the hair-shaved back of a rat, the skin color beneath the test area as well as that outside of the test area was visually observed and measured on Day 1, Day 2, Day 3, Day 4 and Day 5. Skin color change in chromatism ($\Delta a^*$) measured by a Chromometer was recorded. The level of irritation was also observed visually and assigned a value of 0-3. Photographs were also taken at each designated day for visual observation and measurement.

Figure 3:
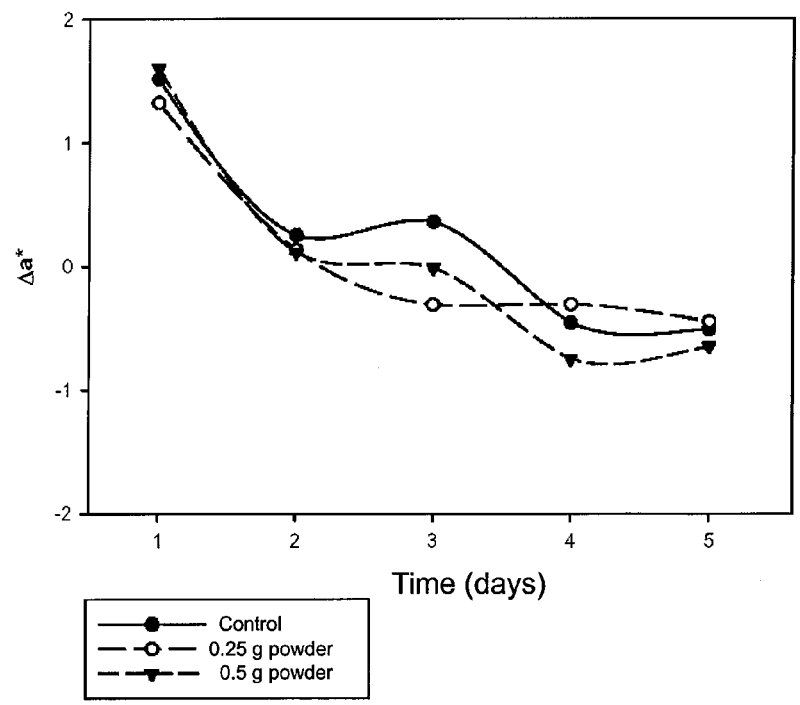
FIG. 3 is a graph showing the irritation effect of an alkylsulfonated chitosan powder according to an embodiment of this invention upon rat skin, in which two different amounts of the alkylsulfonated chitosan powder (0.25 g and 0.5 g per 2.5×2.5 $cm^2$ area) were given in the experimental groups, and no chitosan was given in the control group (for each group, n=6)

Table 3 and FIG. 3 present the results of this experiment. The level of skin irritation as determined chromatographically was highest after the first day for both the experimental groups and the control, indicating the probability of the residual irritation effect caused by shaving or the irritation effect caused by petroleum jelly per se. However, a statistical analysis of the results reveals that no significant difference in skin color change was present amongst the two experimental groups and the control throughout the 5-day experiment (ANOVA test, $p>0.05$). In addition, no skin irritation was observed in any of the tested rats on any day, and the assigned irritation value for visible observation was therefore consistently 0.

TABLE 3

The chromatism and visual observation results of rat skins treated with the alkylsulfonated chitosan of this invention

| | Control | | 0.25 g powder | | 0.5 g powder | |
|---|---|---|---|---|---|---|
| Day | $\Delta a^*$ | Visual | $\Delta a^*$ | Visual | $\Delta a^*$ | Visual |
| 1 | 1.516 (0.534) | 0 | 1.323 (0.411) | 0 | 1.603 (0.403) | 0 |
| 2 | 0.251 (0.456) | 0 | 0.132 (0.314) | 0 | 0.112 (0.201) | 0 |
| 3 | 0.360 (1.361) | 0 | −0.310 (0.410) | 0 | −0.013 (1.330) | 0 |
| 4 | −0.454 (0.883) | 0 | −0.307 (0.256) | 0 | −0.747 (0.717) | 0 |
| 5 | −0.504 (0.730) | 0 | −0.447 (0.717) | 0 | −0.644 (0.519) | 0 |

*Standard deviation is indicated in parentheses. N = 6.

Based on the obtained results, it is concluded that the alkylsulfonated chitosan of this invention has no skin irritation effect to the mammalian skin.

Experiment 4

Evaluation of the Inflammation Effect of Chemically Modified Chitosan of this Invention In this experiment, a powder of an alkylsulfonated chitosan produced according to an embodiment of this invention (a high MW chitosan sulfonated with 1,3-propane sultone) was used.

Human fibroblast cells ATCC 60038 were cultured in vitro and the concentration of prostaglandin-$E_2$ ($PGE_2$), the release of which was used as an indicator of inflammation, was measured through optical density at 405 nm after addition of the alkylsulfonated chitosan of this invention.

Ethanol, which does not inflame fibroblasts and cause release of $PGE_2$, was used as a negative control. Phorbol myristate acetate (PMA), a powerful inflammatory agent, was used as a positive control. In the experimental groups, 0.001%, 0.002%, 0.003% or 0.004% (w/w) of the alkylsulfonated chitosan of this invention was added to the cell culture.

Figure 4:
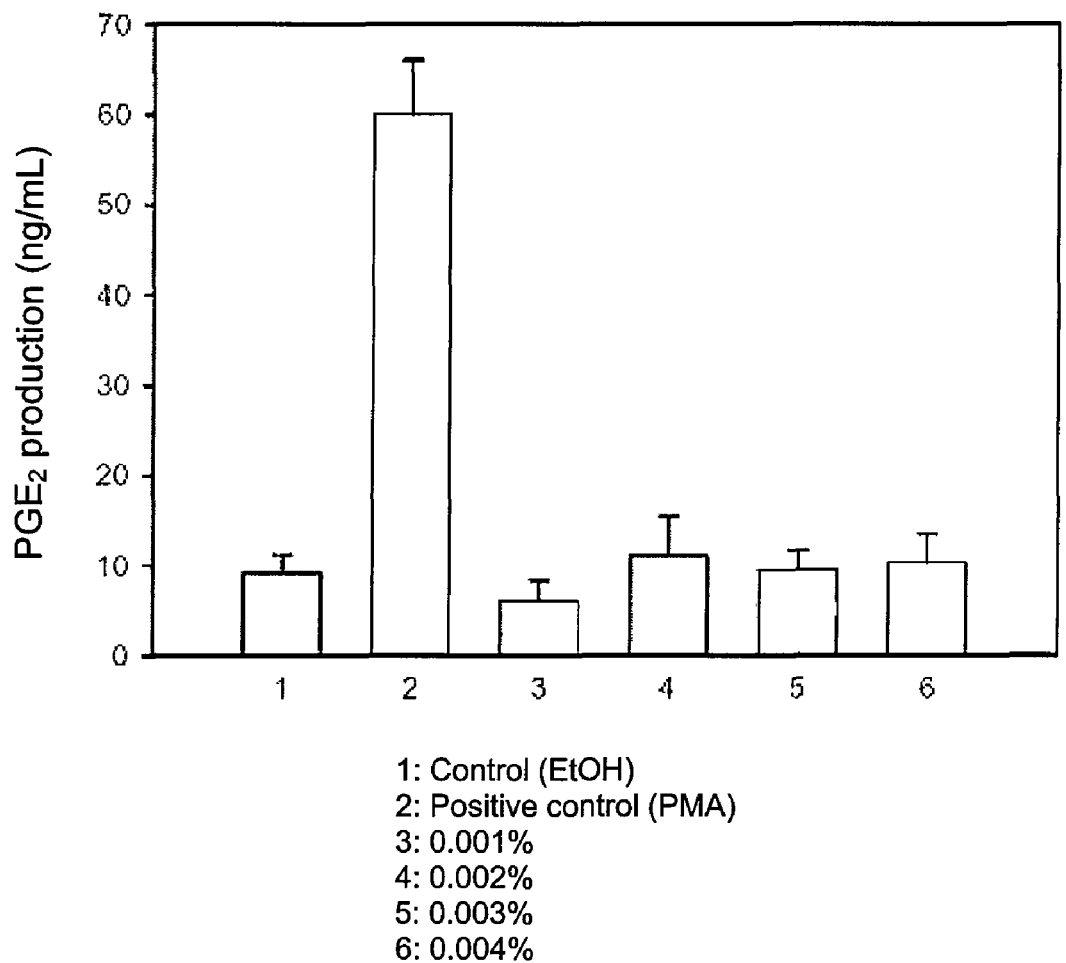
FIG. 4 is a graph showing the inflammatory effect of an alkylsulfonated chitosan according to an embodiment of this invention as measured by prostaglandin-$E_2$ ($PGE_2$) production by human fibroblast cells ATCC 60038, in which the concentration of $PGE_2$ was measured 24 hours after the fibroblasts were treated with the alkylsulfonated chitosan, and the data were represented by mean±standard deviation (for each group, n=6)

FIG. 4 shows the results, which indicate that the alkylsulfonated chitosan of this invention induced no more $PGE_2$ release than ethanol and significantly less than PMA, further confirming that the alkylsulfonated chitosan of this invention is not an inflammatory agent. The results of FIG. 4 also reveal that the alkylsulfonated chitosan of this invention is histocompatible to the human skin.

Experiment 5

Evaluation of the Wound Healing Effect of Chemically Modified Chitosan of this Invention In this and subsequent experiments, a film of alkylsulfonated chitosan produced according to an embodiment of this invention (a high MW chitosan sulfonated with 1,3-propane sultone), which has an 80% degree of sulfonation, was used.

Chitosan sponges used in this and subsequent experiments were prepared by Chinatex by dissolving 5% (w/w) chitosan in a 2 wt % acetic acid$_{(aq)}$ and placing the resultant mixture in a 20 cm×20 cm×0.3 cm container. The mixture was freeze dried, followed by neutralization with 5% NaOH$_{(aq)}$. The thus-obtained product was then washed in deionized water until neutral and freeze dried again.

Chitosan fibers used in this and subsequent experiments were prepared by Chinatex by dissolving 5% (w/w) chitosan in a 2 wt % acetic acid$_{(aq)}$ and filtering the resultant mixture through a metal filter. After degassing, the mixture was added with 5% NaOH$_{(aq)}$ and then wet-spun. The resultant fibers were washed with deionized water until neutral and then dried.

Sprague-Dawley rats weighing around 250-300 g were anesthetized, and their backs were shaved and disinfected. Thereafter, a wound of approximately 3 cm×3 cm and deep to the panniculus carnosus was made using a surgical knife on the hair-shaved back for each rat. A dressing made of alginate (KALTOSTAT®), a chitosan sponge, chitosan fiber, or an alkylsulfonated chitosan film of this invention was then applied to the wound and covered with gauze. A 6 cm×7 cm piece of Tegaderm (3M, Minnesota) was then superposed on the gauze and secured with an elastic bandage wound around the rat. The rats were kept in isolation and supplied with feed and water ad libidum. Healing of the wound was assessed on Day 3, Day 7, Day 14 and Day 21 after operation. The bandages were not replaced during the period of experiment, although they were temporarily removed for inspection.

All dressings appeared to be non-cytotoxic. Repair rate of the panniculus carnosis was calculated by (area of wound immediately after operation−area of wound on Day n)/(area of wound immediately after operation). All dressings exhibited approximately a 70% repair rate 14 days after operation. On Day 21 the repair rates were all almost 100%, except when chitosan fiber was used. However, as clearly shown in FIG. 5, only the wound treated with a dressing made of the alkylsulfonated chitosan film of this invention was fully closed and exhibits far more advanced healing. Therefore, the alkylsulfonated chitosan film of this invention exhibits a superior wound healing effect as compared to alginate or unmodified chitosan.

Experiment 6

Figure 6:
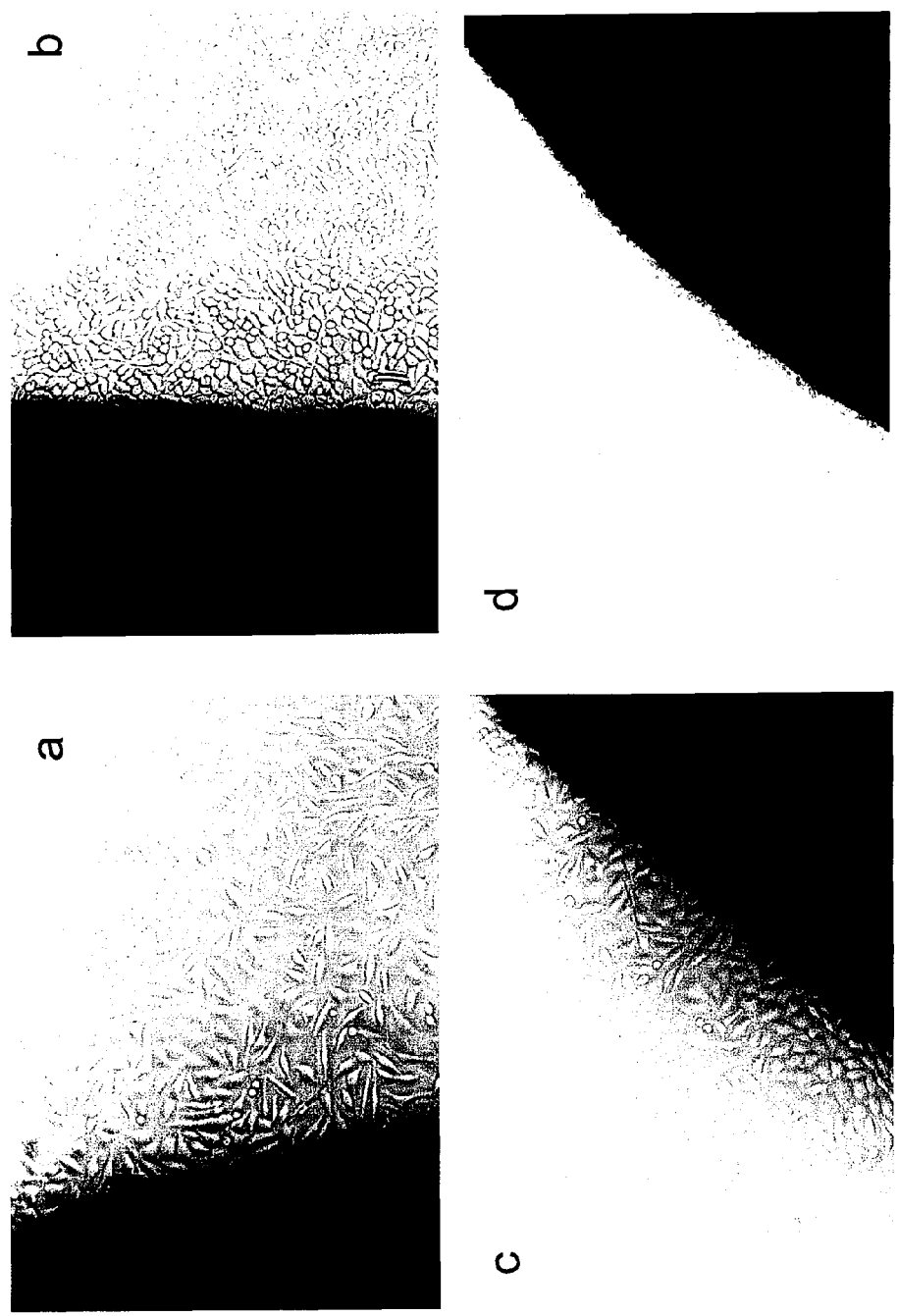
FIG. 6 shows the cellular morphology of mouse fibroblasts L929 grown on a Millipore AP250 1000 filter (a negative control dressing), in which panel a: 1000× magnification; panel b: 100× magnification; panel c: 400× magnification; and panel d; 40× magnification.
Figure 7:
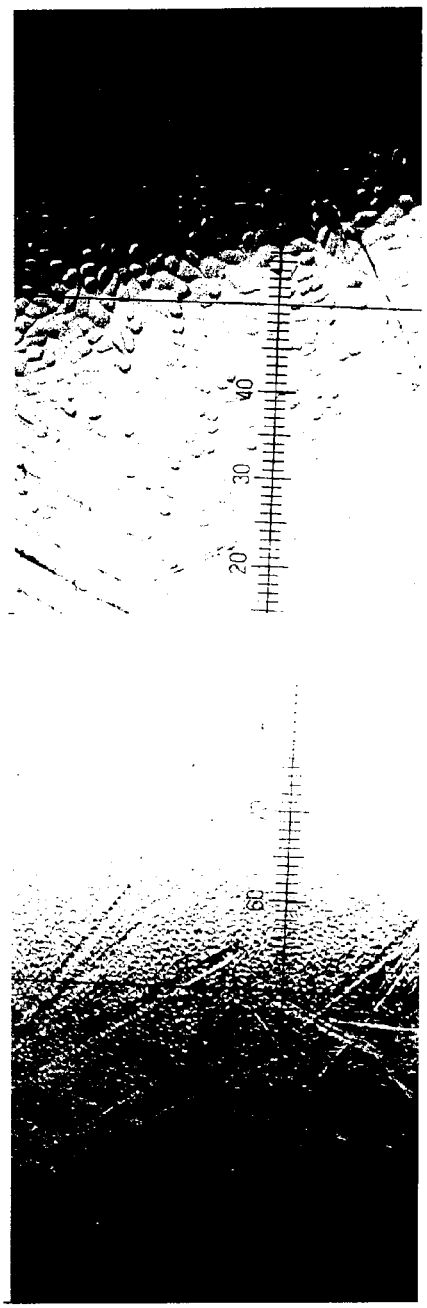
FIG. 7 show the cellular morphology of mouse fibroblasts L929 grown around an experimental dressing, i.e., KALTOSTAT®, in which left panel: 100× magnification; and right panel: 1000× magnification.
Figure 8:
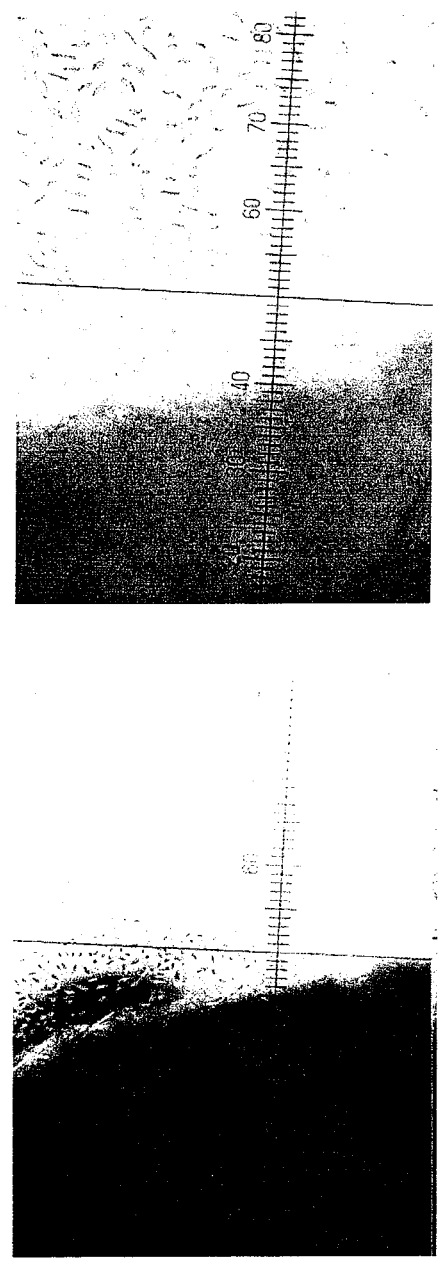
FIG. 8 shows the cellular morphology of mouse fibroblasts L929 grown around an experimental dressing, i.e., an un-modified chitosan sponge, in which left panel: 100× magnification; and right panel: 1000× magnification.

Evaluation of the Biocompatibility and Cytotoxicity Effect of Chemically Modified Chitosan of this Invention Mouse fibroblast cells L929 were cultured to confluence in 6 cm plates. A sterile sample of one of five dressings was added to each plate. The dressings included a control millipore filter (FIG. 6) and four experimental dressings including KALTOSTAT® (FIG. 7), chitosan sponge (FIG. 8), chitosan fiber (FIG. 9), and a 4 mg film made of the alkylsulfonated chitosan of this invention (FIG. 10). Each of the samples was added to the center of the plate, which was then incubated for one day. Cellular morphology was inspected microscopically. The cells grown around the four experimental dressings appeared to have the same morphology as that of the negative control, indicating that the four experimental dressings are all biocompatible.

Histological analysis using 2% crystal violet stain was also performed to determine cytotoxicity. The cells grown around all four dressings were stained with crystal violet which stains only cells (FIGS. 11-14). Since the cell growth around the four experimental dressings was normal, the materials for making said dressings, including the alkylsulfonated chitosan of this invention, are non-toxic.

Experiment 7

Evaluation of the Inhibitory Effect of Chemically Modified Chitosan of this Invention Against *Malassezia furfur*

*Malassezia* is a lipophilic yeast found on skin and body surfaces of humans and animals. It has been shown that colonization with *Malassezia* may occur as early as neonatal period. It is a member of the normal skin flora in as much as 90% of adults and may occasionally cause superficial and deep mycoses.

There are seven proposed species in the genus *Malassezia* based on molecular, morphological, and biochemical profiles. The most common and well-known species are *Malassezia furfur* and *Malassezia pachydermatis*.

*Malassezia furfur* is the causative agent of Pityriasis versicolor, Pityriasis folliculitis, and it has recently been implicated as a causative agent of seborrhoeic dermatitis and dandruff. It has also been recovered in blood cultures from neonate and adult patients undergoing lipid replacement therapy. *M. furfur* is a lipophilic yeast living on the skin as part of the normal flora.

*Malassezia pachydermatis* is a distinctive species due to its well-known zoophilic nature. It causes canine otitis externa and is prevalent in carnivores. However, according to current knowledge, *Malassezia pachydermatis* is not the only *Malassezia* species associated with infections or colonization in animals. Some lipid-dependent species of *Malassezia* may also be isolated as occasional causes of canine otitis externa. *Malassezia pachydermatis* may cause disseminated infections in humans as well.

In this experiment, the applicants examined the inhibitory effect of an alkylsulfonated chitosan (AS-CH) according to an embodiment of this invention (a high MW chitosan sulfonated with 1,3-propane sultone) against *Malassezia furfur*.

*Malassezia furfur* BCRC 32066 was activated by inoculating the same onto a potato dextrose agar slant and then subjecting to cultivation in a 35° C. incubator overnight. A small amount of the colonies grown on the potato dextrose agar slant were taken by an inoculation loop and transferred to 10 mL normal saline (pH=7) and mixed well in a glass tube, so that the yeast cells were evenly distributed in normal saline to form a standard yeast cell solution having a concentration of $1.5 \times 10^8$ cells/mL. The standard solution was 100-fold diluted before use.

To four flasks were respectively added 10 mL of dd water (pH=7). After autoclaving, three flasks were respectively added with an alkylsulfonated chitosan (AS-CH) of the invention to a concentration of 1 mg/mL, 5 mg/mL or 10 mg/mL, and the fourth flask which was not added with anything served as a control group. Thereafter, each of the four flasks was added with 100 μL of the yeast cell solution as prepared above. After shaking at 35° C. for 1 or 2 hours, plating yeast cells onto malt extract agar plates using the solutions of the four flasks were conducted in duplicate. The malt extract agar plates were incubated at 35° C. overnight and observed two days later. The inhibitory activity (%) was calculated according to the following equation:

$$\text{inhibitory activity (\%)} = \frac{\text{colony number of the control group} - \text{colony number of the experimental group}}{\text{colony number of the control group}} \times 100$$

The obtained results of the duplicated experiments are shown in Tables 4 and 5, respectively.

TABLE 4

In vitro inhibitory activity of AS-CH against *M. furfur* BCRC 32066 (Experiment 1)

| Incubation Time (h) | No. of colonies counted on control plate | Inhibition (%) of an added amount of AS-CH | | |
|---|---|---|---|---|
| | | 1 mg/mL | 5 mg/mL | 10 mg/mL |
| 0.2 | 784 | 90.0 | 85.7 | 99.2 |
| 1 | 553 | 99.2 | 98.8 | 99.9 |
| 2 | 706 | 99.9 | 100.0 | 100.0 |

TABLE 5

In vitro inhibitory activity of AS-CH against *M. furfur* BCRC 32066 (Experiment 2)

| Incubation Time (h) | No. of colonies counted on control plate | Inhibition (%) of an added amount of AS-CH | | |
|---|---|---|---|---|
| | | 1 mg/mL | 5 mg/mL | 10 mg/mL |
| 0.2 | 606 | 91.4 | 99.8 | 100.0 |
| 1 | 260 | 99.9 | 100.0 | 100.0 |
| 2 | 142 | 100.0 | 100.0 | 100.0 |

Based on the obtained results, it is concluded that the alkylsulfonated chitosan (AS-CH) of this invention at the lowest concentration (1 mg/mL) can exhibit an excellent effect in inhibiting the growth of *M. furfur* BCRC 32066 even at the shortest contact time of one hour.

*Malassezia pachydermatis* was tested in other experiments, and the alkylsulfonated chitosan (AS-CH) of this invention was proved to be effective in inhibiting the growth thereof, although a higher concentration of the AS-CH and a longer contact time might be used.

Therefore, it is contemplated that the chemically modified chitosan of this invention can be used in the manufacture of products having inhibitory effect on *Malassezia furfur* and/or *Malassezia pachydermatis*.

Experiment 8

Evaluation of the Inhibitory Effect of Chemically Modified Chitosan of this Invention Against *Propionibacterium acnes*

*Propionibacterium acnes* is the causative agent of acne vulgaris (pimples). It is a common resident of the pilosebaceous glands of the human skin. The bacteria release lipases to digest a surplus of the skin oil, sebum, that has been produced. The combination of digestive products (fatty acids) and bacterial antigens stimulates an intense local inflammation that bursts the hair follicle. Then, a lesion forms on the surface of the skin in the form of a pustule (Whitehead). Since acne is caused in part from an infection, it can be suppressed with topical and oral antibiotics such as clindamycin, erythromycin, or tetracycline. Some other forms of therapy include chemicals that enhance skin removal (i.e. benzoyl peroxide) or slow the production of sebum (Retin A and Accutane).

In this experiment, the applicants examined the inhibitory effect of three alkylsulfonated chitosans (a very low MW AS-CH, a low MW AS-CH a high MW AS-CH) produced according to the preferred embodiments of this invention (chitosan sulfonated with 1,3-propane sultone) against *Propionibacterium acnes*, in which an unmodified chitosan (MW around 140,000) was also used for comparison.

A 24-well plate was used for the present experiment. The first well received only 0.5 mL of sterilized water and 0.5 mL of Luria-Bertani broth (LB). The 2nd to 12th wells received 1 mL of sterilized water. The 1st and 2nd wells were then added with 1 mL of a 5 wt % alkylsulfonated chitosan solution$_{(aq)}$. After mixing, 1 mL of the resultant solution in the 2nd well was transferred to the 3rd well and mixed, and 1 mL of the mixed solution in the 3rd well was transferred to the 4th well. A two-fold serial dilution was therefore conducted from the 2nd well to the 12th well in this manner. Thereafter, each of the twelve wells was added with 1 mL of the bacterial culture (a mixture made of 1 mL overnight culture and 100 mL LB medium). The plate was then placed at 37° C. for 24 hrs to allow the growth of the bacterial culture added in each well.

Like Experiment 1, the anti-microbial effect was expressed as minimum inhibitory concentration (MIC) based on OD measurement. The obtained results are summarized in Table 6.

TABLE 6

In vitro inhibitory activity of three different AS-CHs of this invention against *Propionibacterium acnes* as determined by minimum inhibitory concentration (MIC).

| Test compound | MIC (mg/mL) |
|---|---|
| Chitosan | >4.00 mg/mL |
| High MW AS-CH | 3.12 mg/mL |
| Low MW AS-CH | 0.16 mg/mL |
| Very Low MW AS-CH | 0.16 mg/mL |

Based on the obtained results, it is concluded that the alkylsulfonated chitosans (AS-CH) of this invention exhibit a superior effect in inhibiting the growth of *Propionibacterium acnes*.

Therefore, it is contemplated that the chemically modified chitosan of this invention can be used in the manufacture of products having inhibitory effect on *Propionibacterium acnes*, e.g., an anti-acne cream.

Experiment 9

Evaluation of the Skin Hydration Maintenance Effect of Chemically Modified Chitosan of this Invention This experiment was conducted to explore the skin hydration maintenance effect of chemically modified chitosan produced according to this invention, in which an alkylsulfonated chitosan according to an embodiment of this invention (a high MW chitosan sulfonated with 1,3-propane sultone) was used in comparison with hyaluronic acid and collagen.

Prior to experiment, the inner side of a lower arm of a volunteer was washed using a detergent containing no perfume and having no skin hydration maintenance effect and then marked with four circular areas with a diameter of 2.5 cm. 30 minutes later, three of the four circular areas were respectively applied with 30 μL of a test sample (the alkylsulfonated chitosan of this invention, hyaluronic acid and collagen) of equal concentration and the remaining one which was treated with nothing served as a control. The skin hydration conditions of the four areas were examined using a Comeometer CM825PC (Courage and Khazaka, Cologne, Germany) at three different time intervals, i.e., 5, 15 and 30 minutes after application of the test sample.

Figure 15:
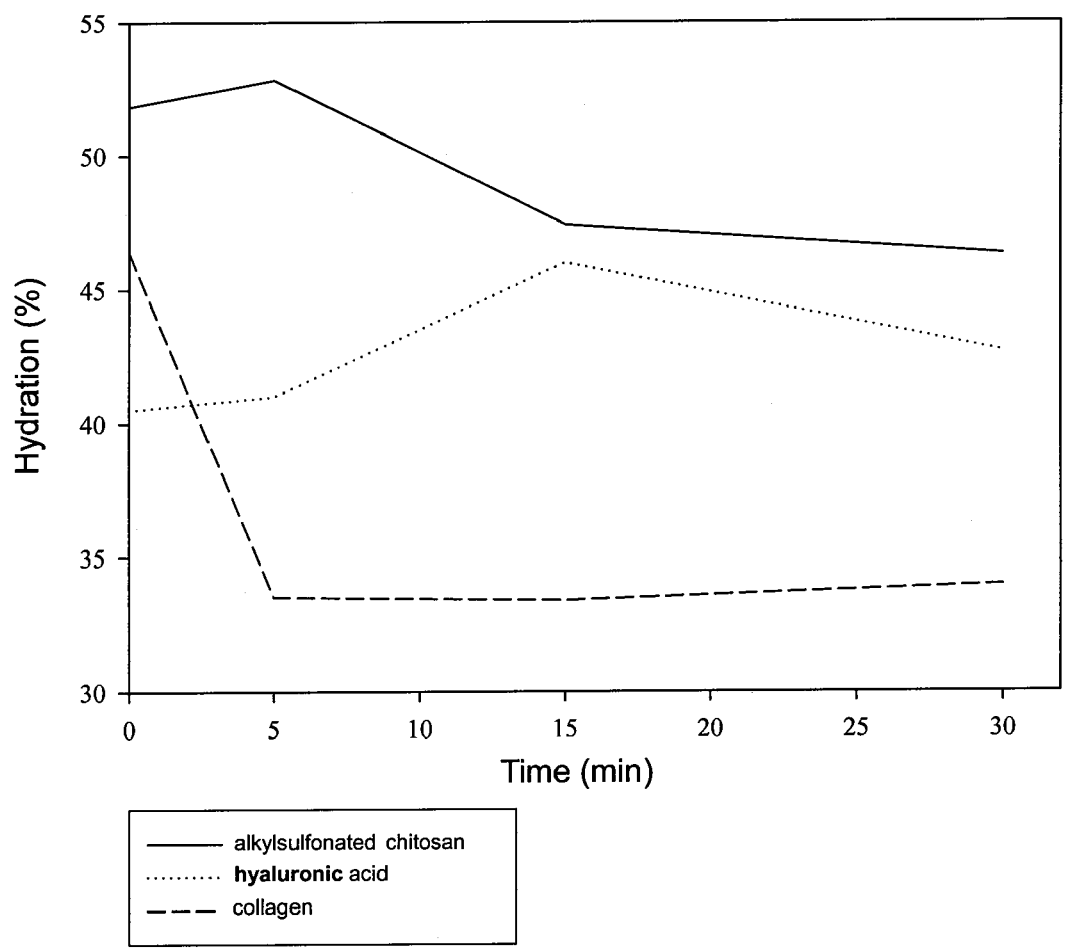
FIG. 15 shows the skin hydration maintenance effect of an alkylsulfonated chitosan according to an embodiment of this invention, as compared to hyaluronic acid and collagen.

The obtained results are shown in FIG. 15. It can be seen that the skin hydration maintenance effects amongst the three test samples are: the alkylsulfonated chitosan of this invention>hyaluronic acid>collagen. Therefore, it is contemplated that the chemically modified chitosan produced according to this invention can be used in the manufacture of products in which the skin hydration maintenance effect is desired.

Experiment 10

Evaluation of the UV Light Absorption Effect of Chemically Modified Chitosan of this Invention This experiment was conducted to explore the UV light absorption effect of chemically modified chitosan produced according to this invention, in which two alkylsulfonated chitosans (a low MW AS-CH and a high MW AS-CH) produced according to the preferred embodiments of this invention were used.

A low MW AS-CH and a high MW AS-CH were dissolved in deionized water to form solutions of different concentrations (2, 5 and 10 wt %), and aliquots (1 mL) of the thus-prepared solutions were respectively placed in quartz tubes. These tubes were then subjected to UV light scanning within wavelengths from 250 nm to 450 nm.

Figure 16:
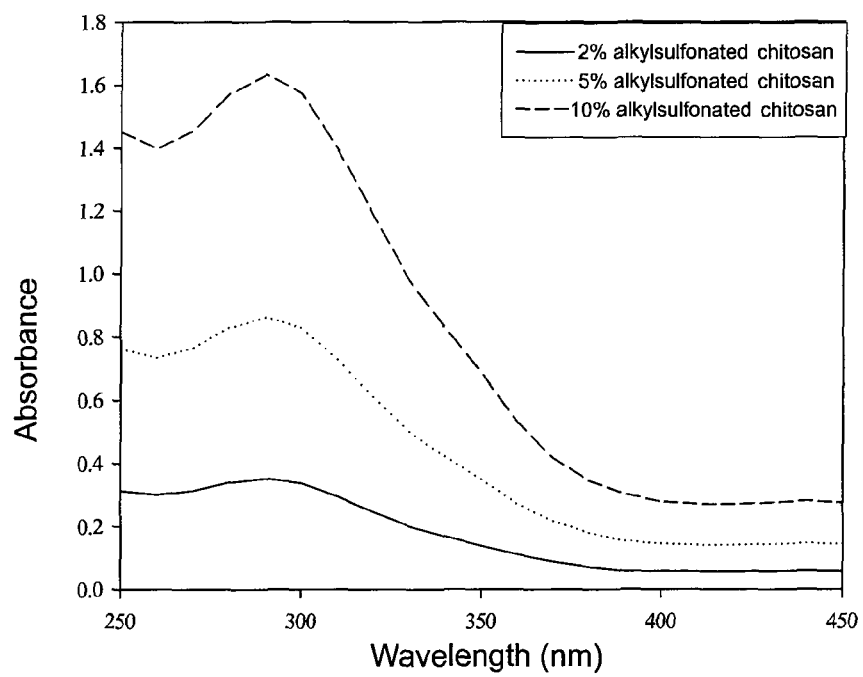
FIG. 16 shows the UV light absorbing ability of a high molecular weight alkylsulfonated chitosan according to an embodiment of this invention tested in three different amounts.
Figure 17:
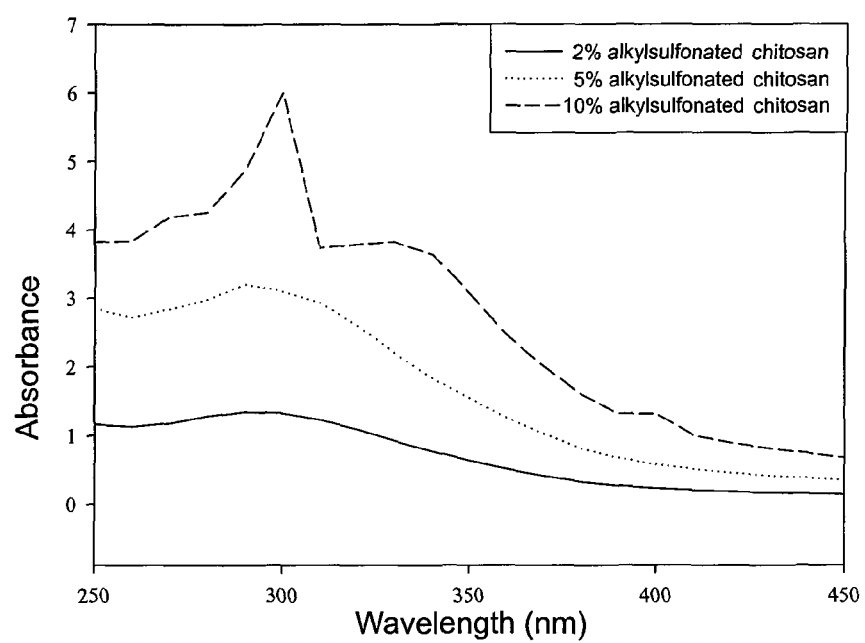
FIG. 17 shows the UV light absorbing ability of a low molecular weight alkylsulfonated chitosan according to an embodiment of this invention tested in three different amounts.

Referring to the results shown in FIGS. 16 and 17, it is clear that the two chemically modified chitosans produced according to this invention exhibit excellent effects in absorbing UVB. Therefore, it is contemplated that the chemically modified chitosans produced according to this invention can act as a UV light absorber in products having UV protective effect, such as sunscreen cream.

Experiment 11

Evaluation of the Effect of Chemically Modified Chitosan of this Invention in Retarding Scent Release This experiment was conducted to explore the effect of chemically modified chitosan produced according to this invention in retarding scent release, in which an alkylsulfonated chitosan according to an embodiment of this invention (a high MW chitosan sulfonated with 1,3-propane sultone) was used.

Figure 18:
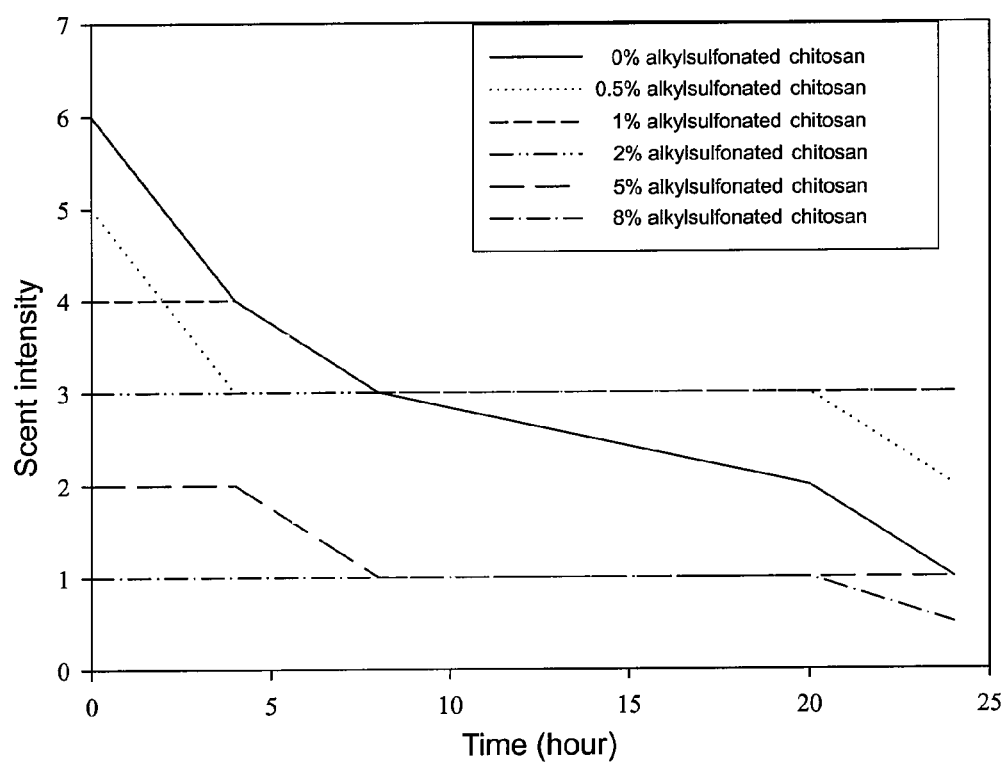
FIG. 18 shows the effect of an alkylsulfonated chitosan according to an embodiment of this invention in retarding the scent release of a tested perfume.

Aliquots (30 μL) of a commercial perfume were respectively added with an alkylsulfonated chitosan of this invention to form even mixtures of different concentrations (0.5, 1, 2, 5 and 8 wt %). Thereafter, an aliquot (30 μL) of each of the thus-prepared samples was dropped onto a perfume smelling strip. The scent release from each perfume smelling strip was detected and scored by five volunteers at designated intervals. The obtained results are shown in FIG. 18.

During a 24-hr detection, it was found that the alkylsulfonated chitosan of this invention at a concentration from 0.5-2 wt % exhibits an excellent sustained-release effect of the perfume. The increased concentration of the alkylsulfonated chitosan of this invention (5-8 wt %) could result in the formation of a film, which prevented the release of scent molecules. Therefore, based on the observed effects, the chemically modified chitosan produced according to this invention can control the release of volatile molecules and therefore can be used in the manufacture of, e.g., odor control products, products requiring sustained-release effect, etc.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A chemically modified polyaminosaccharide comprising a polyaminosaccharide and sulfur, the chemically modified polyaminosaccharide capable of suppressing the depletion of the sulfur content to no more than 3% by weight upon being subjected to the treatment of an alkaline solution, said chemically modified polysaccharide being produced by a process of alkylsulfonating an un-modified polyaminosaccharide having amino functional groups by a hydrocarbyl sultone compound in the presence of an organic solvent under a reflux temperature of the organic solvent, wherein the hydrocarbyl sultone compound has a formula of:

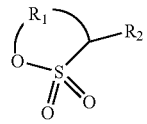

in which
$R_1$ is selected from —$(CH_2)_x$— where x is an integer of 2 to 4 and —CH=CH—; and
$R_2$ is selected from H and a $C_1$-$C_3$ alkyl group; and
wherein the organic solvent has less than 10% water and is selected from the group consisting of methanol, ethanol, isopropanol, butanol methoxypropanol, and combinations thereof;
such that a predetermined proportion of the amino functional groups in the thus-produced chemically modified polyaminosaccharide is alkylsulfonated by the hydrocarbyl sultone compound via a covalent bond.

2. The chemically modified polyaminosaccharide of claim 1, wherein, in the sulfonating process, the un-modified polyaminosaccharide has a predetermined size, and the used amount of the hydrocarbyl sultone compound relative to the number of moles of the amino functional groups of the un-modified polyaminosaccharide is controlled so that the chemically modified polyaminosaccharide has a predetermined degree of sulfonation ranging from 5% to at least 90%.

3. The chemically modified polyaminosaccharide of claim 1, wherein, in the sulfonating process, the un-modified polyaminosaccharide has a predetermined size, and the used amount of the hydrocarbyl sultone compound relative to the number of moles of the amino functional groups of the un-modified polyaminosaccharide is controlled so that the chemically modified polyaminosaccharide has a predetermined degree of sulfonation ranging from 10% to 80%.

4. The chemically modified polyaminosaccharide of claim 1, wherein, in the sulfonating process, the un-modified polyaminosaccharide has a molecular weight between 300 and 1,500,000.

5. The chemically modified polyaminosaccharide of claim 4, wherein, in the sulfonating process, the un-modified polyaminosaccharide has a molecular weight less than 10,000.

6. The chemically modified polyaminosaccharide of claim 4, wherein, in the sulfonating process, the un-modified polyaminosaccharide has a molecular weight between 10,000 and 35,000.

7. The chemically modified polyaminosaccharide of claim 4, wherein, in the sulfonating process, the un-modified polyaminosaccharide has a molecular weight between 35,000 and 140,000.

8. The chemically modified polyaminosaccharide of claim 4, wherein, in the sulfonating process, the un-modified polyaminosaccharide has a molecular weight between 140,000 and 1,500,000.

9. The chemically modified polyaminosaccharide of claim 1, wherein, in the sulfonating process, the un-modified polyaminosaccharide comprises a deacetylated polyaminosaccharide.

10. The chemically modified polyaminosaccharide of claim 1, wherein, in the sulfonating process, the un-modified polyaminosaccharide comprises chitosan.

11. The chemically modified polyaminosaccharide of claim 10, wherein, in the sulfonating process, the chitosan has a degree of deacetylation ranging from 50% to 100%.

12. The chemically modified polyaminosaccharide of claim 1, wherein, in the sulfonating process, the hydrocarbyl sultone compound is selected from 1,3-propane sultone, 1,3-propene sultone, 1,4-butane sultone, 2,4-butane sultone, and combinations thereof.

13. A process for producing a chemically modified polyaminosaccharide, comprising:
   forming a mixture by admixing an organic solvent with an un-modified polyaminosaccharide having amino functional groups;
   alkylsulfonating the un-modified polyaminosaccharide by adding a hydrocarbyl sultone compound to the mixture under a reflux temperature of the organic solvent,
   wherein the hydrocarbyl sultone compound has a formula of:

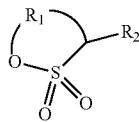

in which
   $R_1$ is selected from —$(CH_2)_x$— (where x is an integer of 2 to 4) and —CH=CH—; and
   $R_2$ is selected from H and a $C_1$-$C_3$ alkyl group; and
   wherein the organic solvent has less than 10% water and is selected from the group consisting of methanol, ethanol, isopropanol, butanol methoxypropanol, and combinations thereof;
   such that a predetermined proportion of the amino functional groups in the thus-produced chemically modified polyaminosaccharide is alkylsulfonated by the hydrocarbyl sultone compound via a covalent bond.

14. The process of claim 13, wherein the un-modified polyaminosaccharide has a molecular weight between 300 and 1,500,000.

15. The process of claim 14, wherein the un-modified polyaminosaccharide has a molecular weight less than 10,000.

16. The process of claim 14, wherein the un-modified polyaminosaccharide has a molecular weight between 10,000 and 35,000.

17. The process of claim 14, wherein the un-modified polyaminosaccharide has a molecular weight between 35,000 and 140,000.

18. The process of claim 14, wherein the un-modified polyaminosaccharide has a molecular weight of between 140,000 and 1,500,000.

19. The process of claim 13, wherein the un-modified polyaminosaccharide comprises a deacetylated polyaminosaccharide.

20. The process of claim 13, wherein the un-modified polyaminosaccharide comprises chitosan.

21. The process of claim 20, wherein the chitosan has a degree of deacetylation ranging from 50% to 100%.

22. The process of claim 13, wherein the hydrocarbyl sultone compound is selected from 1,3-propane sultone, 1,3-propene sultone, 1,4-butane sultone, 2,4-butane sultone, and combinations thereof.

23. The process of claim 13, wherein the chemically modified polyaminosaccharide produced by the process may be further converted to a metal salt form by subjecting it to an alkaline treatment using a metal hydroxide aqueous solution.

24. The process of claim 13, wherein the used amount of the hydrocarbyl sultone compound relative to the number of moles of the amino functional groups of the un-modified polyaminosaccharide is controlled so that the recovered chemically modified polyaminosaccharide has a predetermined degree of sulfonation ranging from 5% to at least 90%.

25. The process of claim 13, wherein the used amount of the hydrocarbyl sultone compound relative to the number of moles of the amino functional groups of the un-modified polyaminosaccharide is controlled so that the recovered chemically modified polyaminosaccharide has a predetermined degree of sulfonation ranging from 10% to 80%.

26. The process of claim 13, wherein the hydrocarbyl sultone compound is used in an amount ranging from one fourth to four times the number of moles of the amino functional groups of the un-modified polyaminosaccharide.

27. The process of claim 13, wherein the thus-formed chemically modified polyaminosaccharide may be recovered by at least one of the following treatments: precipitation, filtration and crystallization.

28. The process of claim 13, wherein the thus-formed chemically modified polyaminosaccharide is recovered in a yield of at least 50%.

29. A composition comprising a chemically modified chitosan and sulfur, the composition capable of suppressing the depletion of the sulfur content to no more than 3% by weight upon being subjected to the treatment of an alkaline solution, the composition being produced by a process of alkylsulfonating an un-modified chitosan having amino functional groups by a hydrocarbyl sultone compound in the presence of an organic solvent under a reflux temperature of the organic solvent,
   wherein the hydrocarbyl sultone compound has a formula of:

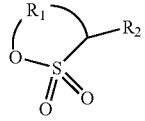

in which
   $R_1$ is selected from —$(CH_2)_x$— (where x is an integer of 2 to 4) and —CH=CH—; and
   $R_2$ is selected from H and a $C_1$-$C_3$ alkyl group; and
   wherein the organic solvent has less than 10% water and is selected from the group consisting of methanol, ethanol, isopropanol, butanol methoxypropanol, and combinations thereof;
   such that a predetermined proportion of the amino functional groups in the thus-produced chemically modified chitosan is alkylsulfonated by the hydrocarbyl sultone compound via a covalent bond.

30. The composition of claim 29, wherein, in the sulfonating process, the un-modified chitosan has a predetermined size, and the used amount of the hydrocarbyl sultone compound relative to the number of moles of the amino functional groups of the un-modified chitosan is controlled so that the chemically modified chitosan has a predetermined degree of sulfonation ranging from 5% to at least 90%.

31. The composition of claim 29, wherein, in the sulfonating process, the un-modified chitosan has a predetermined size, and the used amount of the hydrocarbyl sultone compound relative to the number of moles of the amino functional groups of the un-modified chitosan is controlled so that the chemically modified chitosan has a predetermined degree of sulfonation ranging from 10% to at least 80%.

32. The composition of claim 29, wherein, in the sulfonating process, the un-modified chitosan has a molecular weight between 300 and 1,600,000.

33. The composition of claim 32, wherein, in the sulfonating process, the un-modified chitosan has a molecular weight less than 10,000.

34. The composition of claim 32, wherein, in the sulfonating process, the un-modified chitosan has a molecular weight between 10,000 and 35,000.

35. The composition of claim 32, wherein, in the sulfonating process, the un-modified chitosan has a molecular weight between 35,000 and 140,000.

36. The composition of claim 32, wherein, in the sulfonating process, the un-modified chitosan has a molecular weight between 140,000 and 1,500,000.

37. The composition of claim 29, wherein, in the sulfonating process, the un-modified chitosan has a degree of deacetylation ranging from 50% to 100%.

38. The composition of claim 29, wherein, in the sulfonating process, the hydrocarbyl sultone compound is selected from 1,3-propane sultone, 1,3-propene sultone, 1,4-butane sultone, 2,4-butane sultone, and combinations thereof.

39. The composition of claim 29, which is in a form selected from the group consisting of aqueous solution, film and powder.

40. The composition of claim 29, which has at least one of the following properties: promoting wound healing, inhibiting the growth of microorganisms, having no toxic effect to mammals, having no skin irritation effect to mammals, having no inflammatory effect to mammals, absorbing UV light, maintaining skin hydration, histocompatibility to human skin, and controlling the release of volatile molecules.

41. The composition of claim 29, which has the property of inhibiting the growth of a microorganism selected from streptomycin-resistant *Staphylococcus aureus*, *E. coli*, *Pseudomonas aeruginosa*, *Candida albicans*, *Malassezia furfur*, *Malassezia pachydermatis*, *Propionibacterium acnes*, and combinations thereof.

42. A product selected from the group consisting of a personal care product, a food product, a cleaning product, an agricultural product, a cosmetic product, a medicinal product, a medical device, a fabric product, a product for water-treatment, and a biochemical product, the product being manufactured using the composition of claim 29.

43. An odor control product, which is manufactured using the composition of claim 29.

44. A product selected from the group consisting of an anti-microbial agent, a wound dressing, and a UV light absorber, the product being manufactured using the composition of claim 29.

45. A method of promoting wound healing in a mammal in need of such treatment, comprising applying the composition of claim 29 to a mammal having a wound.

46. The method of claim 45, wherein the application of the composition of claim 29 can inhibit fibroplasia due to the healing of the wound of the mammal.

47. The method of claim 45, wherein the wound of the mammal is selected from the group consisting of an open wound, a bleeding wound, a wound caused by transplantation of a vascular graft, a wound caused by transplantation of a vascular patch, a bleeding sutured area, a bleeding cardiac valve area, and combinations thereof.

48. The method of claim 47, wherein the mammal has a wound caused by a transplanted vascular graft and the application of the composition of claim 29 can promote tissue regeneration of the transplanted vascular graft.

49. The method of claim 45, wherein the composition to be applied to the wound is in a form selected from the group consisting of a film, a fiber, a sponge, a gel, a cream, a grease, a spray, a foam, a non-woven fabric, a liquid, a powder, and a dressing.

* * * * *